United States Patent
Eggers

(10) Patent No.: US 10,531,942 B2
(45) Date of Patent: Jan. 14, 2020

(54) ABSORBABLE VASCULAR FILTER

(75) Inventor: Mitchell Donn Eggers, Pearland, TX (US)

(73) Assignee: ADIENT MEDICAL, INC., Pearland, TX (US)

(*) Notice: Subject to any disclaimer, the term of this patent is extended or adjusted under 35 U.S.C. 154(b) by 164 days.

(21) Appl. No.: 13/403,790

(22) Filed: Feb. 23, 2012

(65) Prior Publication Data

US 2013/0226222 A1 Aug. 29, 2013

Related U.S. Application Data

(63) Continuation-in-part of application No. 13/096,049, filed on Apr. 28, 2011, now abandoned, and a continuation-in-part of application No. 13/036,351, filed on Feb. 28, 2011, now abandoned.

(51) Int. Cl.
*A61F 2/01* (2006.01)

(52) U.S. Cl.
CPC ......... *A61F 2/01* (2013.01); *A61F 2002/011* (2013.01); *A61F 2002/016* (2013.01)

(58) Field of Classification Search
CPC ......... A61F 2/01; A61F 2/90; A61F 2002/016
USPC ............................... 606/200; 623/1.11, 1.15
See application file for complete search history.

(56) References Cited

U.S. PATENT DOCUMENTS

| | | |
|---|---|---|
| 4,425,905 A | 1/1984 | Simon |
| 4,655,771 A | 4/1987 | Wallsten |
| 4,817,600 A | 4/1989 | Herms et al. |
| 5,317,612 A | 5/1994 | Bryan et al. |
| 5,350,398 A | 9/1994 | Pavcnik et al. |
| 5,375,612 A * | 12/1994 | Cottenceau et al. ......... 128/899 |
| 5,443,498 A | 8/1995 | Fontaine |
| 5,591,199 A | 1/1997 | Porter et al. |
| 5,626,605 A | 5/1997 | Irie et al. |

(Continued)

FOREIGN PATENT DOCUMENTS

| | | |
|---|---|---|
| CA | 2093599 A1 | 10/1993 |
| CA | 2710001 A1 | 7/2009 |

(Continued)

OTHER PUBLICATIONS

Eriksen et al. "Choice of mesh for laparoscopic ventral hernia repair." Hernia (2007) 11:481-492.*

(Continued)

*Primary Examiner* — Sarah A Simpson
(74) *Attorney, Agent, or Firm* — Pillsbury Winthrop Shaw Pittman LLP

(57) ABSTRACT

An absorbable vascular filter is disclosed for deployment within a vessel for temporary filtering of body fluids. A preferred embodiment is the placement of such absorbable vascular filter within the inferior vena cava (IVC) to filter emboli for the prevention of pulmonary embolism for a limited duration in time. Once protection from PE is complete, the filter is biodegraded according to a planned schedule determined by the absorption properties of the filter components. Hence the temporary absorbable vascular filter obviates the long term complications of permanent IVC filters such as increased deep vein thrombosis, neighboring organ puncture from filter fracture and embolization while also circumventing the removal requirement of metal retrievable IVC filters.

17 Claims, 13 Drawing Sheets

(56) References Cited

U.S. PATENT DOCUMENTS

| | | | |
|---|---|---|---|
| 6,127,600 A | 10/2000 | Beach et al. | |
| 6,146,404 A | 11/2000 | Kim et al. | |
| 6,159,142 A * | 12/2000 | Alt | 600/3 |
| 6,245,103 B1 | 6/2001 | Stinson | |
| 6,258,026 B1 | 7/2001 | Ravenscroft et al. | |
| 6,267,776 B1 | 7/2001 | O'Connell | |
| 6,497,709 B1 | 12/2002 | Heath | |
| 6,506,205 B2 | 1/2003 | Goldberg et al. | |
| 6,517,559 B1 | 2/2003 | O'Connell | |
| 6,582,447 B1 | 6/2003 | Patel et al. | |
| 6,620,183 B2 | 9/2003 | Dimatteo | |
| 6,652,558 B2 | 11/2003 | Patel et al. | |
| 6,658,558 B1 | 12/2003 | Kahle et al. | |
| 6,792,979 B2 | 9/2004 | Konya et al. | |
| 6,932,832 B2 | 8/2005 | Patel et al. | |
| 6,972,025 B2 * | 12/2005 | WasDyke | 606/200 |
| 7,001,424 B2 | 2/2006 | Patel et al. | |
| 7,261,731 B2 | 8/2007 | Patel et al. | |
| 7,279,005 B2 * | 10/2007 | Stinson | A61F 2/90 623/1.22 |
| 7,582,108 B2 | 9/2009 | Hierlemann et al. | |
| 8,162,970 B2 | 4/2012 | Gilson et al. | |
| 2001/0021871 A1 | 9/2001 | Stinson | |
| 2003/0014127 A1 | 1/2003 | Talja et al. | |
| 2003/0040771 A1 * | 2/2003 | Hyodoh et al. | 606/200 |
| 2003/0139765 A1 | 7/2003 | Patel et al. | |
| 2003/0153945 A1 | 8/2003 | Patel et al. | |
| 2003/0163159 A1 | 8/2003 | Patel et al. | |
| 2003/0176888 A1 | 9/2003 | O'Connell | |
| 2003/0199918 A1 | 10/2003 | Patel et al. | |
| 2004/0059373 A1 | 3/2004 | Shapiro et al. | |
| 2004/0138738 A1 * | 7/2004 | Stinson | A61F 2/90 623/1.38 |
| 2004/0193209 A1 | 9/2004 | Pavcnik et al. | |
| 2005/0143805 A1 * | 6/2005 | Hierlemann et al. | 623/1.15 |
| 2005/0267512 A1 | 12/2005 | Osborne et al. | |
| 2005/0267515 A1 | 12/2005 | Oliva et al. | |
| 2006/0025852 A1 | 2/2006 | Armstrong | |
| 2006/0206138 A1 | 9/2006 | Eidenschink | |
| 2006/0241675 A1 * | 10/2006 | Johnson | A61F 2/01 606/200 |
| 2007/0032816 A1 | 2/2007 | O'Connell et al. | |
| 2007/0093744 A1 | 4/2007 | Elmaleh | |
| 2007/0112372 A1 | 5/2007 | Sosnowski et al. | |
| 2008/0027481 A1 * | 1/2008 | Gilson et al. | 606/200 |
| 2008/0107744 A1 | 5/2008 | Chu | |
| 2008/0119886 A1 * | 5/2008 | Greenhalgh | A61B 17/0057 606/200 |
| 2008/0269871 A1 | 10/2008 | Eli | |
| 2009/0099643 A1 | 4/2009 | Hyodoh et al. | |
| 2009/0105747 A1 | 4/2009 | Chanduszko et al. | |
| 2009/0187210 A1 * | 7/2009 | Mackiewicz | A61F 2/01 606/200 |
| 2009/0192543 A1 | 7/2009 | Wasdyke | |
| 2009/0299403 A1 | 12/2009 | Chanduszko et al. | |
| 2010/0016881 A1 | 1/2010 | Fleck et al. | |
| 2010/0042135 A1 | 2/2010 | Shirley et al. | |
| 2010/0087908 A1 | 4/2010 | Hilaire et al. | |
| 2010/0174310 A1 | 7/2010 | Tessmer | |
| 2010/0256669 A1 | 10/2010 | Harris et al. | |
| 2010/0268262 A1 | 10/2010 | Balar | |
| 2011/0106234 A1 | 5/2011 | Grandt | |
| 2011/0213404 A1 | 9/2011 | Binkert | |
| 2011/0301633 A1 | 12/2011 | Muck et al. | |
| 2012/0245620 A1 | 9/2012 | Gilson et al. | |
| 2012/0259402 A1 | 10/2012 | Grandt | |
| 2012/0277787 A1 | 11/2012 | Eggers | |

FOREIGN PATENT DOCUMENTS

| | | |
|---|---|---|
| CN | 101945675 A | 1/2011 |
| EP | 0894505 A2 | 2/1999 |
| EP | 1574169 A3 | 9/2005 |
| EP | 1582178 A2 | 10/2005 |
| JP | 2002-535075 A | 10/2002 |
| JP | 2008-508073 A | 3/2008 |
| JP | 2009-518122 A | 5/2009 |
| JP | 2009-543655 A | 12/2009 |
| WO | 1996017634 A2 | 6/1996 |
| WO | 2000/044308 A2 | 8/2000 |
| WO | 2006/020425 A1 | 2/2006 |
| WO | 2007/067451 A2 | 6/2007 |
| WO | 2008/010197 A2 | 1/2008 |
| WO | 2009/085548 A2 | 7/2009 |
| WO | 2010/077973 A2 | 7/2010 |

OTHER PUBLICATIONS

Mitchell Donn Eggers, U.S. Appl. No. 13/036,351, filed Feb. 28, 2011.
International Application No. PCT/US2012/026398, International Search Report dated May 24, 2012.
Australian Government IP Application Patent No. 2012223607, Patent Examination Report No. 1, dated Jan. 30, 2015.
Zhenling, J, et al., "Type of hernia repair material, research work development and application selection", Journal of Southeast University (Medical Science Edition), 2009, 5(28):451-454.
English Machine Translation of Abstract for Zhenling, J, et al., "Type of hernia repair material, research work development and application selection", Journal of Southeast University (Medical Science Edition), 2009, 5 (28):451-454.
Goldhaber S Z, Ortel T L. The Surgeon General's Call to Action to Prevent Deep Vein Thrombosis and Pulmonary Embolism, Office of the Surgeon General (US), National Heart, Lung, and Blood Institute (US),Rockville (MD), 2008, pp. 1-42.
Spencer F A, Emery C, Lessard D, Anderson F, Emani S, Aragam J et al., "The Worcester Venous Thromboembolism study; A Population-Based Study of the Clinical Epidemiology of Venous Thromboembolism", J Gen Intern Med Jul. 2006; 21 (7); pp. 722-727.
Bick R L., "Hereditary and acquired thrombophilia: preface", Seminars in Thrombosis and Hemostasis, 1999; vol. 25, No. 3, pp. 251-253.
Agudelo J F, Morgan S J, Smith W R., "Venous Thromboembolism in Orthopedic Trauma Patients", Orthopedics. Oct. 2005; 28(10):1164-1171.
Tapson V F., "Acute pulmonary embolism", N Engl J Med, 2008, 358, 10. pp. 1037-1052.
Goldhaber S Z, Visani L, De Rosa M. "Acute P E: clinical outcomes in the International Cooperative Pulmonary Embolism Registry (ICOPER)", Lancet 1999. 353. pp. 1386-1389.
Geerts W H, Jay R M, Code KI, et al. "A comparison of low-dose heparin with low-molecular weight heparin as prophylaxis against venous thromboembolism after major trauma", N Engl J. Med. 1996; 335:701-707.
Silverstein D M, Heit J A, Mohr D N, Petterson T M, O'Fallon W M, Meltron L J, 3rd. "Trends in the incidence of deep vein thrombosis and pulmonary embolism: a 25-year population-based study", Arch Intern Med 1998; 158(6). 585-593.
Von V R. Weitereuntersuchungenueber die verstopfung der lungenarterien and ihrefolge. Traube's Beitraegeexp Path u Physiol, 1846; 2:21-31.
Goldhaber S Z, Savage D D, Garrison R J, et al. Risk factors for pulmonary embolism: The Framingham Study. Am J. Med. 1983; 74: 1023-1028.
Coon W W. Epidemiology of venous thromboembolism. Ann Surg. 1977; 186:149-164.
Muntz J E, Michota F A. Prevention and management of venous thromboembolism in the surgical patient: options bye surgery type and individual patient risk factors, Am J of Surg, 2010; 199, S11-20.
American Academy of Orthopaedic Surgeons Clinical Guideline on Prevention of Pulmonary Embolism in Patients Undergoing Total Hip or Knee Arthroplasty, American Academy of Orthopaedic Surgeons, May 2007, pp. 1-63.
Pulmonary Embolism Prevention (PEP) Trial Collaborative Group: Prevention of pulmonary embolism and DVT with low dose aspirin: pulmonary embolism prevention (PEP) trial. Lancet. 2000; 355: pp. 1295-1302.

(56) References Cited

OTHER PUBLICATIONS

Prins M H, Hutten B A, Koopman M M, et al. Longterm treatment of venous thromboembolic disease. Thromb Haemost 1999;82:892-898.
Tran H, McRae S, Ginsberg J. Anticoagulant Treatment of Deep Vein Thrombosis and Pulmonary Embolism. Cardiology Clinics, 2008, 26, 235-250.
Morgan S J, Jeray K J, Phieffer L S, Grisby J H, Bosse M J, Kellam J F. Attitudes of orthopaedic trauma surgeons regarding current controversies in the management of pelvic and acetabular fractures. J Orthop Trauma. 2001; 15:526-532.
Meissner M H, Chandler W L, Elliot J S. Venous thromboembolism in trauma: a local manifestation of systemic hypercoagulability? J. Trauma 2003; 4:224-231.
Geerts W H, Bergqvist D, Pineo G F, et al. Prevention of venous thromboembolism: American College of Chest Physicians evidence-based clinical practice guidelines (8th edition). Chest 2008; 133:381S-453S.
Huo M H, Spyropoulos A C. The eighth American college of chest physicians guidelines on venous thromboembolism prevention: implications for hospital prophylaxis strategies. J Thromb Thrombolysis. Feb. 2011; 31(2): 196-208.
Baglin T P, Brush J, Streiff M. Guidelines on the use of vena cava filters. British Committee for Standard in Haematology, British J of Haematology, 2006, 134, 590-595.
Rogers F B, Cipolle M D, Velmahos G, et al. Practice management guidelines for the prevention of venous thromboembolism in trauma patients: the East practice management guidelines work group. J. Trauma. 2002; 53:142-164.
Rosenthal D, Wellons E D, Lai K M, et al. Retrievable inferior venal cava filters: initial clinical results. Ann Vasc Surg 2006; 20:157-165.
Gosin I S, Graham A M, Ciocca R G, et al. Efficacy of prophylactic vena cava filters in high risk trauma patients. Ann Vasc Surg 1997; 11:100-105.
Spain D A, Richardson J D, Polk H C, et al. Routine prophylactic vena cava filter insertion in severely injured patients decreases the incidence of pulmonary embolism. J Am Coll Surg 1995; 180:641-647.
Stein P D, Kayali F, Olson R E. Twenty-one year trends in the use of inferior vena cava filters. Arch Intern Med 2004; 164:1541-1545.
Kaufman J A, Kinney T B, Streiff M D, et al. Guidelines for the use of retrievable and convertible vena cava filters: report from the Society of Interventional Radiology multidisciplinary consensus conference. J Vasc Intery Radiol. 2006; 17:449-459.
Rodriquez J L, Lopez J M, Proctor M C, et al. Early placemen of prophylactic vena cava filters in injured patients at high risk for pulmonary embolism. J. Trauma. 1996; 40:797-804.
Langan E M III, Miller R S, Caset W J III, Carsten C G III, Graham R M, Taylor S M. Prophylactic inferior vena cava filters in trauma patients at high risk: follow-up examination and risk/benefit assessment. J Vasc Surg. 1999; 30:484-490.
Greenfield L J, Proctor M C, Rodriquez J L, Luchette F A, Cipolle M D, Cho J. Posttrauma thromboembolism prophylaxis. J. Trauma. 1997, 42:100-103.
Young T, Tang H, Hughes R. Vena cava filters for the prevention of pulmonary embolism (Review). The Cochrane Library 2010, Issue 2.
Decousus H, Leizorovics A, Parent F, et al. A clinical trial of vena caval filters in the prevention of pulmonary embolism in patients with proximal deep-vein thrombosis, N England J. Med. 338, 7:409-415.
The PREPIC Study Group. Eight-year follow-up of patients with permanent vena cava filters in the prevention of pulmonary embolism: the PREPIC randomized study. Circulation 2005; 112:416-422.
Ray C E, Kaufman J A. Complications of vena cava filters. Abdom Imaging 1996; 21:368-374.
Ballew K A, Philbrick J T, Becker D M. Vena cava filter devices. Clin Chest Med 1995; 16:295-305.
Streiff M B. Vena cava filters: a comprehensive review. Blood 2000; 95:3669-3677.
Pons M, Riglietti A, van den Berg J C. The role of vena cava filters in the management of venous thromboembolism. J Cardiovasc Surg 2010; 51: 355-364.
Usoh F, Hignorani A, Ascher E, et al. Long-term follow-up for superior vena cava filter placement. Ann Vasc Surg. 2009; 23:350-354.
Turba U C, Arsian B, Meuse M, et al. Gunther Tulip filter retrieval experience: predictors of successful retrieval. Cardiovase Intervent Radiol. 2009.
Kinney T B. Update on inferior vena cava filters. J Vasc Intery Radiol. 2003; 14:425-440.
Grande W J, Trerotola S O, Reilly P M, et al. Experience with the recovery filter as a retrievable inferior vena cava filter. J Vasc Intery Radiol 2005; 16:1189-1193.
Kirilcuk N N, Herget E J, Dicker R A, et al. Are temporary inferior vena cava filters really temporary? Am J Surg 2005; 190:858-863.
Kumar B C, Chakraverty Z, Zealley I. Failed retrieval of potentially retrievable IVC filters: a report of two cases. Cardiovasc Intervent Radiol 2006; 29: 126-127.
Removing Retrievable Inferior Vena Cava Filters: Initial Communication. FDA Division of Small Manufacturers, International and Consumer Assistance, Aug. 9, 2010.
Nicholson W, Nicholson W J, Tolerico P, et al. Prevalence of fracture and fragment embolization of Bard retrievable vena cava filters and clinical implications including cardiac perforation and tamponade. Arch Intern Med. 2010, pp. 1827-1831.
Karmy-Jones R, Jurkovich G H, Velmahos G C, et al. Practice patterns and outcomes of retrievable vena cava filters in trauma patients: an AAST multicenter study. J. Trauma. 2007; 62: 17-25.
Tschoe M, Kim H S, Brotman D J, et al. Retrievable vena cava filters: a clinical review. J Hosp Med 2009, 4; 7: 441-448.
Dabbagh O, Nagam N, Chitima-Matsiga R, et al. Retrievable inferior vena cava filters are not getting retrieved Where is the gap? Thrombosis Rsch 2010. 126: 493-497.

\* cited by examiner

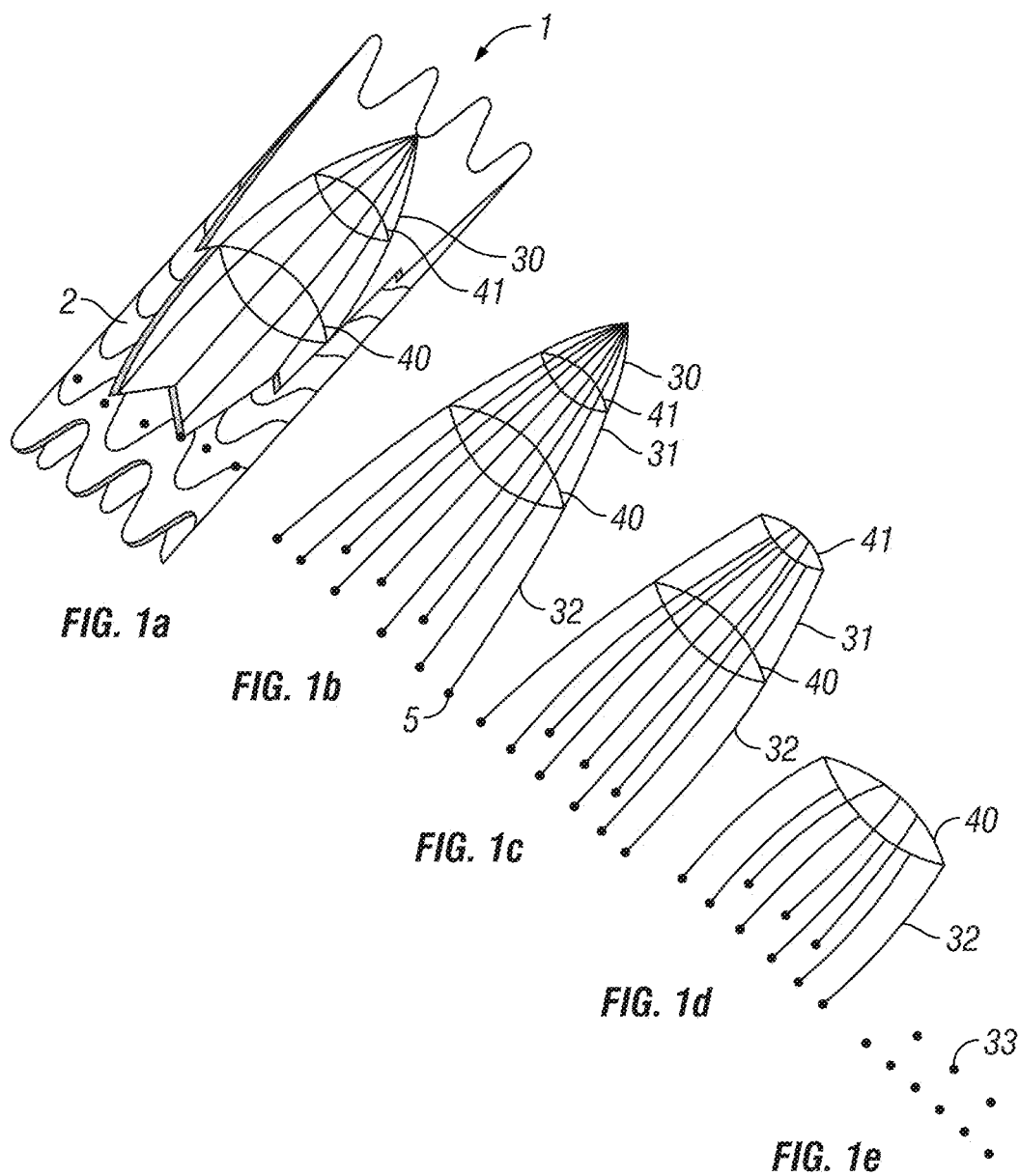

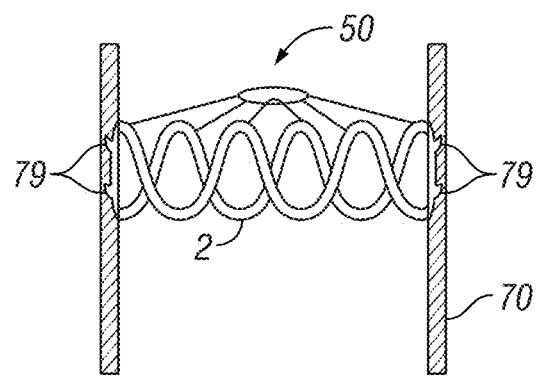
*FIG. 2a*
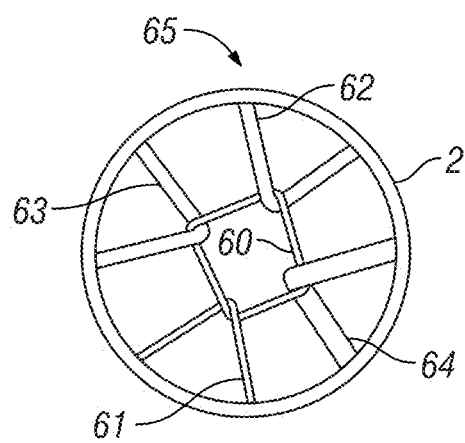
*FIG. 2b*
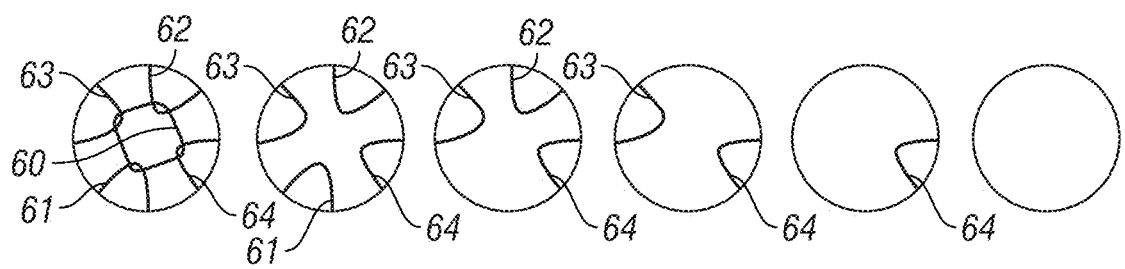
*FIG. 2c*   *FIG. 2d*   *FIG. 2e*   *FIG. 2f*   *FIG. 2g*   *FIG. 2h*

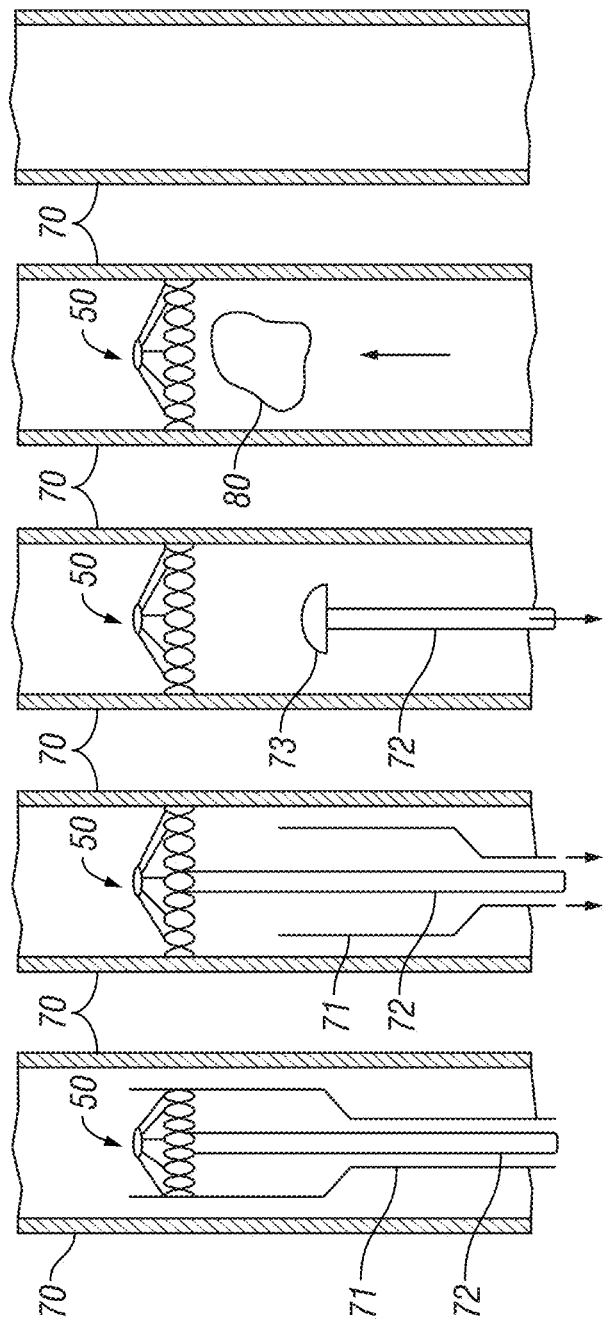

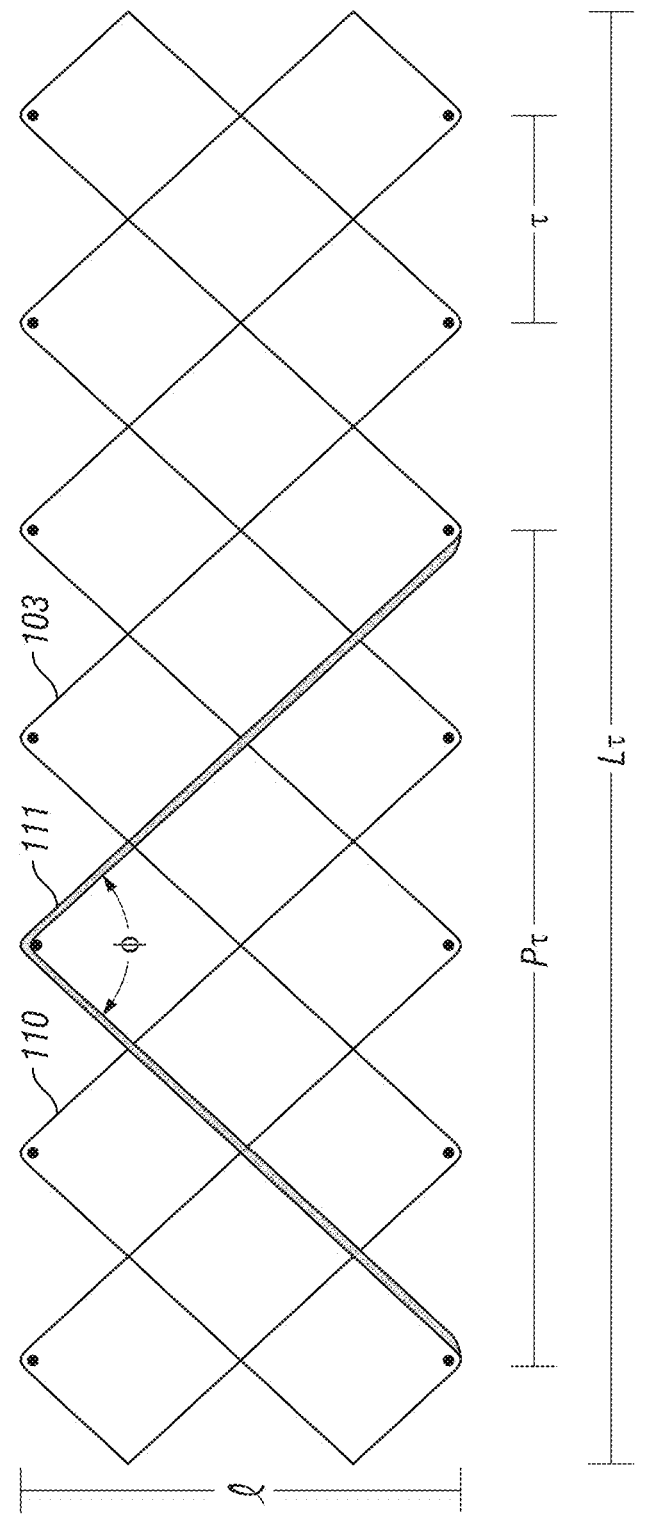

ABSORBABLE VASCULAR FILTER

CROSS-REFERENCE TO RELATED APPLICATIONS

This application is a continuation-in-part application of U.S. patent application Ser. No. 13/036,351, filed Feb. 28, 2011, and is a continuation-in-part application of U.S. patent application Ser. No. 13/096,049, filed Apr. 28, 2011, all of which applications are expressly incorporated herein by reference in their entirety.

FIELD OF THE INVENTION

The present invention relates generally to a vascular filter and more particularly to an absorbable vascular filter deployed within a vessel for temporary filtering of body fluids. A preferred embodiment is the placement of such absorbable vascular filter within the inferior vena cava (IVC) for the prevention of pulmonary embolisms for a specific duration of time determined by the absorption properties of the filter.

BACKGROUND OF THE INVENTION

Between 100,000 to 300,000 Americans die annually from pulmonary embolism (PE)—more than breast cancer and AIDS combined—representing the 3rd leading cause of death in the US [1-5]. A similar incidence of PE is found in Europe with approximately 370,000 annual deaths [6]. Moreover, PE is the 3rd most common cause of death in trauma patients that survive the first 24 hours. An estimated 25% of all hospitalized patients have some form of deep vein thrombosis (DVT) which is often clinically unapparent unless PE develops [7]. On average, 33% of DVT will progress to symptomatic PE of which 10% will be fatal [6].

The US Surgeon General has recognized this alarming statistic and in 2008 issued a formal Call to Action to Prevent DVT and PE [1]. Unfortunately, DVT/PE disproportionately affects the elderly, in part due to prolonged periods of inactivity following medical treatment. The incidence is relatively low under the age of 50 (1/100,000), then accelerates exponentially reaching 1000/100,000 by the age of 85 [8]. Consequently the US Surgeon General has proclaimed that the growth in number of DVT/PE cases with an aging US population may outpace the population growth in the absence of better prevention [1].

Risk factors for PE arising from DVT follow Virchow's Triad [9]: (i) endothelial injury, (ii) hypercoaguability, and (iii) hemodynamic changes (stasis or turbulence). Hence specific risk factors include hip and knee arthroplasty, abdominal, pelvic and extremity surgeries, pelvic and long bone fractures, prolonged immobility such as prolonged hospital stays and air travel, paralysis, advanced age, prior DVT, cancer, obesity, COPD, diabetes and CHF. Orthopedic surgeons are especially concerned since their patients carry a 40%-80% risk for DVT and PE following knee and hip surgeries in the absence of prophylactic treatment [10-12].

The American Academy of Orthopaedic Surgeons (AAOS) has issued guidelines for PE prophylaxis. Basically, patients at standard risk should be considered for chemoprophylactic agents such as aspirin, low molecular weight heparin (LMWH), synthetic pentassaccharides, or warfarin, in addition to intra-operative and/or immediate postoperative mechanical prophylaxis [13].

Aspirin has a 29% relative risk reduction in symptomatic DVT and a 58% relative risk reduction in fatal PE [14]. LMWH carries a 30% risk reduction in DVT and has been proven more effective than unfractionated heparin in high risk groups such as hip and knee arthroplasty [7]. Warfarin started within 24 to 48 hours of initiating heparin with a goal of achieving international normalized ratio (INR) results between 2 and 3 as secondary thromboprophylaxis for 3 months reduces the risk of recurrent venous thromboembolism (VTE) by 90% as compared with placebo [15,16]. Mechanical prophylaxis, consisting of pneumatic compression devices that repeatedly compress the legs with an air bladder, are also utilized in conjunction with anticoagulants to reduce the occurrence of PE.

The duration of prophylaxis depends on the source of potential DVT. Current recommendations for prophylaxis consist of a minimum 7-10 days for moderate to high risk surgeries and up to 28-35 days for many orthopedic surgeries. Specifically for orthopedic trauma, DVT prophylaxis is continued until patient mobilization (32%), inpatient discharge (19%), 3 weeks postop (16%), 6 weeks postop (27%), and in rare circumstances greater than 6 weeks (7%) [17]. Studies indicate that hypercoaguability persists for at least one month after injury in 80% of trauma patients [18]. Regarding total knee and hip arthroplasty and cancer surgeries, 35 day prophylactic treatment is recommended [12, 19]. Overall, prophylactic treatment for possible VTE is often warranted for up to 6 weeks following trauma or major surgery.

Contraindications for chemoprophylaxis include active bleeding, hemorrhagic diathesis, hemorrhagic stroke, neurologic surgery, excessive trauma, hemothorax, pelvic or lower extremity fractures with intracranial bleeding, anticoagulation interruption, and recent DVT/PE patients undergoing surgery.

For patients who are contraindicated for the above-mentioned anti-coagulation prophylaxis, or where anti-coagulation therapy has failed, the AAOS, American College of Physicians, and the British Committee of Standards in Haematology all recommend the use of inferior vena cava (IVC) filters [13, 20, 21]. These intravascular metal filters are deployed via catheter into the IVC to essentially catch emboli arising from DVT before reaching the lungs resulting in PE. Furthermore, the British Committee of Standards in Hematology recommends IVC filter placement in pregnant patients who have contraindications to anticoagulation and develop extensive VTE shortly before delivery (within 2 weeks).

The Eastern Association for Surgery of Trauma further recommends prophylactic IVC filters placed in trauma patients who are at increased risk of bleeding and prolonged immobilization [22]. Such prophylactic recommendation follows studies that demonstrate a low rate of PE in patients with severe polytrauma who underwent IVC placement [23-25]. In fact the fastest growing indication of overall IVC filter usage, from 49,000 in 1999 to 167,000 in 2007 with a projected 259,000 units for 2012, is the prophylactic market utilizing retrievable IVC filters [26, 27].

Example vascular filters primarily for IVC placement are disclosed in U.S. Pat. Nos. 4,425,908; 4,655,771, 4,817,600; 5,626,605; 6,146,404; 6,217,600 B1; 6,258,026 B1; 6,497,709 B1; 6,506,205 B2; 6,517,559 B1; 6,620,183 B2; U.S. Pat. App. Pub. No. 2003/0176888; U.S. Pat. App. Pub. No. 2004/0193209; U.S. Pat. App. Pub. No. 2005/0267512; U.S. Pat. App. Pub. No. 2005/0267515; U.S. Pat. App. Pub. No. 2006/0206138 A1; U.S. Pat. App. Pub. No. 2007/0112372 A1; U.S. Pat. App. Pub. No. 2008/0027481 A1; U.S. Pat. App. Pub. No. 2009/0192543 A1; U.S. Pat. App. Pub. No. 2009/0299403 A1; U.S. Pat. App. Pub. No. 2010/0016881

A1; U.S. Pat. App. Pub. No. 2010/0042135 A1; and U.S. Pat. App. Pub. No. 2010/0174310 A1.

IVC filter efficacy has been demonstrated in several class I and II evidence studies [22, 28-30]. Most of the earlier filters installed were expected to be permanent fixtures since endothelialization occurs within 7-10 days making most models impractical to remove without irreversible vascular damage leading to life threatening bleeding, dissection of the IVC, and thrombosis. Although these permanent filters have prevented PE, they have been shown to actually increase the risk of recurrent DVT over time.

Specifically, a Cochrane review [31] on the use of IVC filters for the prevention of PE cites a level I randomized prospective clinical trial by Decousus et al. [32] wherein the incidence of DVT with the IVC filter cohort increased almost 2-fold: (i) 21% incidence of recurrent DVT in the filter cohort vs. 12% in the non-filter LMWH cohort at 2 years (p=0.02), and (ii) 36% incidence of recurrent DVT in the filter cohort vs. 15% in the non-filter group at 8 years (p=0.042) [33]. However, the filters did reduce the occurrence of PE; the filter cohort experiencing only 1% PE vs. the non-filter cohort posting 5% PE in the first 12 days (p=0.03). No statistically significant difference in mortality rate was seen in any time frame investigated. Apparently the initial benefit of reduced PE with permanent IVC filters is offset by an increase in DVT, without any difference in mortality.

In addition to increased incidence of DVT for prolonged IVC filter deployment, filter occlusion has been reported with a 6% to 30% occurrence, as well as filter migration (3% to 69%), venous insufficiency (5% to 59%), and post thrombotic syndrome (13% to 41%) [34-36]. Complications from insertion including hematoma, infection, pneumothorax, vocal cord paralysis, stroke, air embolism, misplacement, tilting arteriovenous fistula, and inadvertent carotid artery puncture have an occurrence rate of 4%-11% [37].

Temporary or retrievable IVC filters have been marketed more recently intended to be removed once the risk of PE subsides, and hence circumvent many of the deleterious complications of permanent filters. The retrievable filters feature flexible hooks, collapsing components, and unrestrained legs to ease retrieval. Unfortunately these same features have led to unwanted filter migration, fatigue failure, IVC penetration, fragment migration to hepatic veins and pulmonary arteries, filter tilt, and metallic emboli [38-43]. Since 2005, 921 adverse filter events have been reported to the FDA including 328 device migrations, 146 device detachments (metallic emboli), 70 perforations of the IVC, and 56 filter fractures [44]. Some retrievable brands post alarming failure rates such as the Bard Recovery filter with 25% fracturing over 50 months which embolized end organs. 71% of the fractures embolized to the heart caused life threatening ventricular tachycardia, tamponade, and sudden death in some cases. An alternative retrievable model, Bard G2, resulted in 12% fractures over 24 months [45]. Such prevalence of device fractures is postulated to be directionally proportional to indwell time.

These failures and others prompted the FDA in August 2010 to issue a formal communication stating that "FDA recommends that implanting physicians and clinicians responsible for the ongoing care of patients with retrievable IVC filters consider removing the filter as soon as protection from PE is not longer needed" [44]. Even though these types of retrievable filters are intended to be removed in months time, several studies indicate that approximately 70%-81% of patients with retrievable IVC filters fail to return to the hospital for filter removal, thereby exposing hundreds of thousands of patients to the life-threatening adverse events of prolonged retrievable IVC filter placement [41, 44, 46-48]. These patients are either lost to follow-up, or refuse to have the filters removed in the absence of complications.

BRIEF SUMMARY OF THE INVENTION

The present invention comprises systems and methods for filtering fluids. Certain embodiments comprise a novel absorbable vascular filter that temporarily prevents pulmonary embolism by capturing and restraining emboli within a body vessel. The absorbable vascular filter, according to certain aspects of the invention, possesses various advantages over all conventional vascular filters, including permanent, temporary, and optional IVC filters. Most importantly, the absorbable vascular filter disclosed herein is slowly biodegraded within the vessel according to a planned schedule engineered by the choice of absorbable filter materials which prevents the requirement of filter removal. Moreover, the absorbable vascular filter elements are manufactured from non-metallic synthetic polymers which do not adversely impact end organs upon carefully planned degradation as exhibited by conventional metal IVC filters that migrate and often become fractionated. Also due to the relative short indwell time (months) of the absorbable vascular filter, the paradoxical increase in DVT seen with conventional long-term IVC filters is likely circumvented.

BRIEF DESCRIPTION OF THE DRAWINGS

FIG. 1a is a cut-away isometric view of one embodiment of the absorbable vascular filter that includes phased sequential biodegradation of the absorbable capture elements.

FIG. 1b features the capture elements of FIG. 1a in detail.

FIG. 1c features the capture elements of FIG. 1b at a later point in time wherein the proximal portion of the capture elements has been bioabsorbed/biodegraded.

FIG. 1d features the capture elements of FIG. 1c at a later point in time wherein the proximal and middle sections of the capture elements have been bioabsorbed/biodegraded, leaving only the distal section.

FIG. 1e represents complete bioabsorption/biodegradation of the capture elements of FIG. 1b at the most distant point in time.

FIG. 2a is a cross-sectional schematic of another embodiment of the absorbable vascular filter that also features phased sequential biodegradation of the absorbable capture elements.

FIG. 2b is an enlarged end-view of the absorbable capture elements of the absorbable filter depicted in FIG. 2a.

FIG. 2c depicts the capture elements of FIG. 2b at the time of filter installation in a vessel.

FIG. 2d depicts the capture elements of FIG. 2c at a later point in time wherein the inner capture ring element has been bioabsorbed/biodegraded.

FIG. 2e depicts the capture elements of FIG. 2d at a later point in time wherein a circumferential-mounted capture element has been bioabsorbed/biodegraded.

FIG. 2f depicts the capture elements of FIG. 2e at a later point in time wherein two circumferential-mounted capture elements have been bioabsorbed/biodegraded.

FIG. 2g depicts the capture elements of FIG. 2f at a later point in time wherein only one circumferential-mounted capture element remains following bioabsorption/biodegradation.

FIG. 2h depicts the capture elements of FIG. 2b which have completely been bioabsorbed/biodegraded at the most distant point in time.

FIG. 9a is a cross-sectional schematic revealing a preferred method for installing the absorbable vascular filter using a catheter-based system with the filter in compressed mode.

FIG. 9b is a cross-sectional schematic detailing the deployment of the absorbable vascular filter using a catheter-based system with sliding outer sheath to deploy the filter in the fully expanded mode.

FIG. 9c is a cross-sectional schematic detailing the removal of the central stabilizing rod or piston used to stabilize the absorbable vascular filter while removing the outer sheath of the catheter-based installation system.

FIG. 9d illustrates the operation of the absorbable vascular filter in the presence of an embolus in the vessel.

FIG. 9e represents the vessel following complete biodegradation/bioabsorption of the absorbable vascular filter.

FIG. 10b is the associated top view of the absorbable vascular filter shown in FIG. 10a.

FIG. 11 is an expanded view of the braid or weave of absorbable elements comprising the stent section of the absorbable vascular filter.

FIG. 13b is an end-view photograph of the integrated absorbable IVC filter presented in FIG. 13a.

DETAILED DESCRIPTION OF THE INVENTION

Figure 3A:
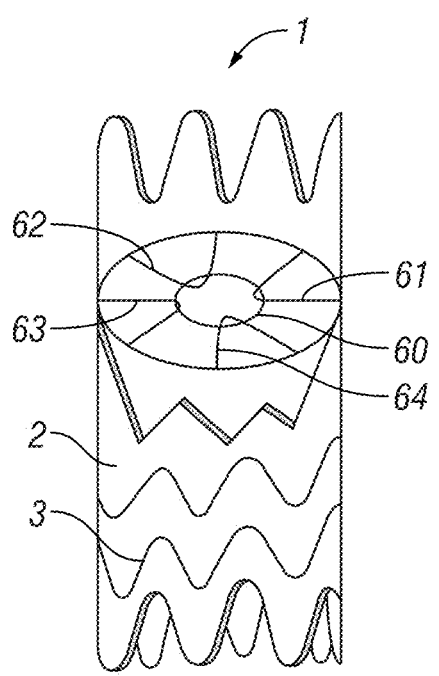
FIG. 3a is a cut-away isometric view of one embodiment of the vascular filter that includes a plurality of capture elements attached to the stent for filtering substances such as emboli.

Embodiments of the present invention will now be described in detail with reference to the drawings and pictures, which are provided as illustrative examples so as to enable those skilled in the art to practice the invention. Notably, the figures and examples below are not meant to limit the scope of the present invention to a single embodiment, but other embodiments are possible by way of interchange of some or all of the described or illustrated elements. Wherever convenient, the same reference numbers will be used throughout the drawings to refer to same or like parts. Where certain elements of these embodiments can be partially or fully implemented using known components, only those portions of such known components that are necessary for an understanding of the present invention will be described, and detailed descriptions of other portions of such known components will be omitted so as not to obscure the invention. In the present specification, an embodiment showing a singular component should not be considered limiting; rather, the invention is intended to encompass other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the components referred to herein by way of illustration.

Referring to the embodiment depicted in FIGS. 1a-e, an absorbable vascular filter 1 consists of an outer, circumferential element 2 for supporting a plurality of absorbable filter capture elements (30-32, 40-41). The capture elements are purposely designed to be biologically absorbed and/or degraded preferably in a sequential manner to avoid simultaneous detachment of the entire filter causing an unexpected embolus. Sequential degradation can be controlled by the choice of absorbable polymers that possess different absorption profiles, diameter, and/or expiration dates. Additionally, absorptive linkages may be incorporated to serves as detachment points during absorption. The sequential bioabsorption/biodegradation is illustrated in FIGS. 1b-e where decomposition begins with the proximal capture elements 30, progressing to the middle section capture elements 31, and finally full bioabsorption/biodegradation as depicted in FIG. 1e.

Such engineered, sequential bioabsorption/biodegradation of the capture elements can be achieved with numerous synthetic materials. The goal is to select the absorbable filter materials to match a desired filter indwell time. Per the prior background section, a filter indwell time of 6 weeks would be suitable for an IVC filter to prevent PE following trauma or in conjunction with major surgeries. Synthetic materials which can be used to form the capture elements include:

Polydioxanone (PDO, PDS)—colorless, crystalline, biodegradable synthetic polymer of multiple repeating etherester units. In suture form, PDS II (Ethicon, Somerville, N.J.) size 4/0 and smaller maintains 60%, 40%, and 35% of its tensile strength at 2, 4, and 6 weeks respectively. For PDS II size 3/0 and larger, it retains 80%, 70%, and 60% of its tensile strength at 2, 4, and 6 weeks respectively. In addition to providing wound support for 6 weeks, PDS II suture is fully absorbed in 183-238 days via hydrolysis making it a strong candidate for IVC filter applications. Basically absorption is minimal in the first 90 days and is essentially complete in 6 months. Finally, PDS has a low affinity for microorganisms and possesses minimal tissue reaction.

Polytrimethylene carbonate (Maxon)—similar to PDS in absorption profile yet with slightly higher breaking strength. Maxon (Covidien, Mansfield, Mass.) maintains 81%, 59%, and 30% of its tensile strength at 2, 4, and 6 weeks respectively, and is fully hydrolyzed in 180-210 days.

Polyglactin 910 (Vicryl)—braided multifilament coated with a copolymer of lactide and glycolide (polyglactin 370). In suture form, Vicryl (Ethicon) size 6/0 and larger maintains 75%, 50%, and 25% of its tensile strength at 2, 3, and 4 weeks respectively and is fully absorbed in 56-70 days.

Polyglycolic acid (Dexon)—similar to Polyglactin, made from polyglycolic acid and coated with polycaprolate. Dexon has similar tensile strength and absorption profile as Polyglactin.

Poliglecaprone 25 (Monocryl)—synthetic copolymer of glycolide and e-caprolactone. Monocryl (Ethicon) maintains 50%-70% and 20%-40% of its tensile strength at 1 and 2 weeks respectively and is fully absorbed in 91-119 days.

Polylacticoglycolic acid (PLGA) copolymer of monomers glycolic acid and lactic acid. Different forms and properties of PLGA can be fabricated by controlling the ratio of lactide to glycolide for polymerization. Like the other synthetic absorbable materials, PLGA degrades by hydrolysis with the absorption profile dependent on the monomer ratio; the higher content of glycolide, the faster degradation. However, the 50:50 copolymer exhibits the fastest degradation at 2 months. Since the polymer degrades in the body to produce lactic acid and glycolic acid, both being normal physiological substances, PLGA poses minimal systemic toxicity.

Poly L-lactic Acid (PLA) is also a polymer made from lactic acid yet with considerable longevity. In soft tissue approximation, PLA remains intact for 28 weeks, and is fully absorbed within 52 weeks.

As an example of engineering capture elements to sequentially degrade following the period of PE protection, the proximal capture elements 30,41 could be fabricated with PDS II size 4/0 (0.15 mm dia.), while the middle capture elements 31,40 fabricated with size 2/0 (0.3 mm dia.), and finally the distal capture elements 32 fabricated with size 2 (0.5 mm) PDS II suture.

As an alternative to assembling a plurality of capture elements, the vascular filter can be fabricated with absorbable or non-absorbable composite mesh. Candidates for a mesh capture system include polypropylene such as C-QUR (Atrium Medical Corp. Hudson N.H.), polypropylene encapsulated by polydioxanone as in PROCEED (Ethicon, Somerville, N.J.), polypropylene co-knitted with polyglycolic acid fibers as in Bard Sepramesh I P Composite (Davol, Inc., Warwick, R.I.), polyethylene terephathalate as in Parietiex Composite (Covidien, Mansfield, Mass.), and ePTFE used in DUALAMESH (W. Gore & Assoc. Inc., Flagstaff, Ariz.).

Figure 3B:
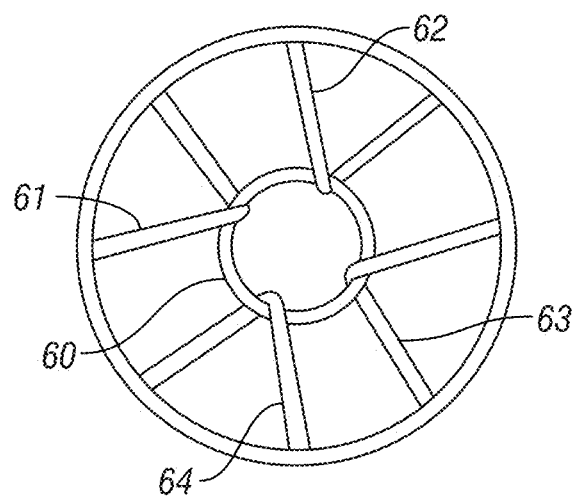
FIG. 3b features the capture elements of FIG. 3a in detail.

Regarding the circumferential element 2 in FIGS. 1, 2, and 3 that serves to support the capture elements of the absorbable vascular filter and maintain filter positioning within the vessel upon expansion from a catheter, either an absorbable material such as described above or non-absorbable material can be utilized. A non-absorbable material would essentially serve as a permanent stent, lasting well beyond the life of the absorbable capture elements. This may be an important option in cases where the vessel needs assistance in maintaining patency. Both types of circumferential elements 2 may incorporate barbs 79 (refer FIG. 2) to maintain filter positioning upon deployment. Plausible non-absorbing materials for constructing the circumferential element include: Nitinol, Elgiloy, Phynox, 316 stainless steel, MP35N alloy, titanium alloy, platinum alloy, niobium alloys, cobalt alloys, and tantalum wire.

FIGS. 2a-2h illustrate another embodiment of the absorbable vascular filter wherein the absorbable capture elements 60-64 are mounted to a simple circumferential element 2 held against the vessel wall 70 with optional barbs 79. Here again the circumferential element 2 can be fabricated with absorbable or non-absorbable materials of the like described above. An enlarged cross-sectional view of the capture element assembly 65 is shown in FIG. 2b. Notice that the sequential degradation of the capture elements is achieved by varying the diameter of the chosen absorbable material. For example, the inner capture element 60 could be PDS II 4/0 (0.15 mm dia.) resulting in the fastest absorption as illustrated in FIG. 2d at time $t_1$, followed by capture element 61 degradation being PDS II 3/0 (0.20 mm dia.) at time $t_2$ in FIG. 2e, followed by capture element 62 degradation being PDS II 2/0 (0.30 mm dia.) at time $t_3$ in FIG. 2f, followed by capture element 63 degradation being PDS II 0 (0.35 mm dia.) at time $t_4$ in FIG. 2g, and finally the degradation of the last capture element 64 constructed of PDS II 1 (0.40 mm dia.) at time $t_5$ in FIG. 2h. Although these dimensions represent a specific example, any diameters within approximately 0.1 mm to 0.7 mm would suffice. Overall, a gradual progression of degradation is designed purposely following a prophylactic window of 6 weeks for trauma and major surgery applications.

Referring to the embodiment depicted in FIGS. 3a and b, a vascular filter 1 consists of an outer, circumferential stent 2 for supporting a plurality of collapsible filter capture elements (60-64) and to maintain vessel patency. The capture elements are purposely designed to be collapsible for catheter-based installation and to avoid end organ damage. The supporting stent 2 is shown to be fabricated as an artificial vascular graft supported by undulating supporting structures 3. This vascular filter, which can be comprised of absorbable or non-absorbable filter capture elements, possesses various advantages over all conventional vascular filters, including permanent, temporary, and optional IVC filters. Most importantly, the vascular filter is fabricated with a stent that serves as a circumferential mount for the capture elements in addition to providing vessel patency, and avoids endothelialization characteristic of metal filters with barbed struts. Hence the increased incidence of DVT observed with metal IVC filters due to inherent vessel damage from the metal struts is likely obviated.

The circumferential stent element 2 in FIG. 3a serves to support the capture elements of the vascular filter, in addition to maintaining vessel patency and maintaining stationary filter positioning within the vessel upon expansion. Numerous types of stents conventionally employed as thoracic endoprostheses can be utilized. Such stents would include Gore TAG, Medtronic Talent and Valiant Systems, and Cook Zenith TX2 System. In particular, the Gore TAG is comprised of an artificial vascular graft fabricated with a fluoropolymer (expanded polytetrafluoroethylenee PTFE and fluorinated ethylene propylene or FEP) combined with a Nitinol supporting structure. Alternatively, the stent component of the vascular filter can be fabricated with only the supporting structure (without the artificial vascular graft) utilizing nickel-titanium alloy (Nitinol), cobalt-chromium-nickel alloy (Elgiloy), cobalt-chromium-nickel-molybdenum alloy (Phynox), 316 stainless steel, MP35N alloy, titanium alloy, platinum alloy, niobium alloys, cobalt alloys, and tantalum wire.

Figure 4A:
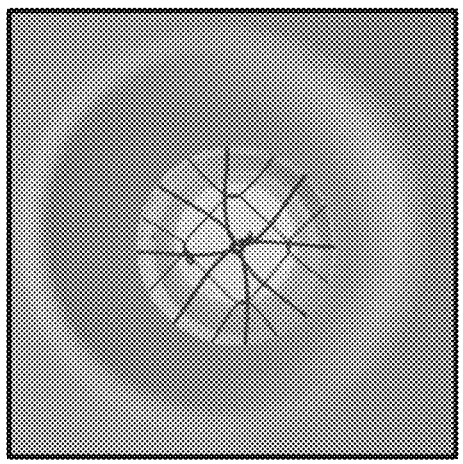
FIG. 4a is an absorbable vascular filter constructed from polydioxanone suture sizes 3-0, 2-0, 0, and 1 in a webbed pattern that features sequential degradation based on the varying diameters and expiration dates of the capture elements.

A specific embodiment of an absorbable vascular filter with sequential degradation was constructed, tested, and evaluated with assorted polydioxanone sutures (sizes 3-0, 2-0, 0, and 1) and is shown in FIG. 4a. The filter featured higher density webbing than shown in FIG. 2b to catch smaller emboli. Polydioxanone was the preferred candidate polymer based on tension retention and absorption properties proven in wound approximation applications. Tygon long flex lifetime tubing (Saint-Gobain Performance Plastics, Akron, Ohio) with 25.4 mm id similar to the IVC was utilized for the vessel wall wherein polydioxanone was fabricated into the various filter patterns shown.

Figure 4B:
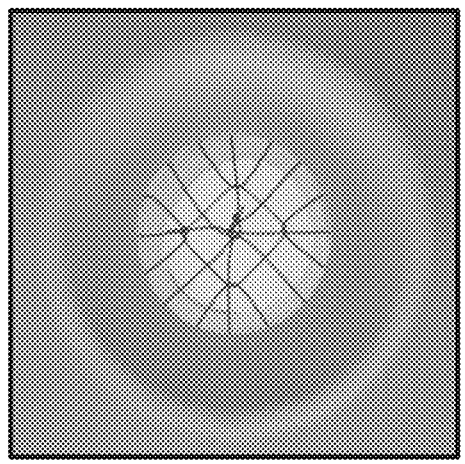
FIG. 4b is an absorbable vascular filter constructed from polydioxanone suture similar in design to the webbed design in FIG. 4a except that only size 2-0 is utilized.
Figure 4C:
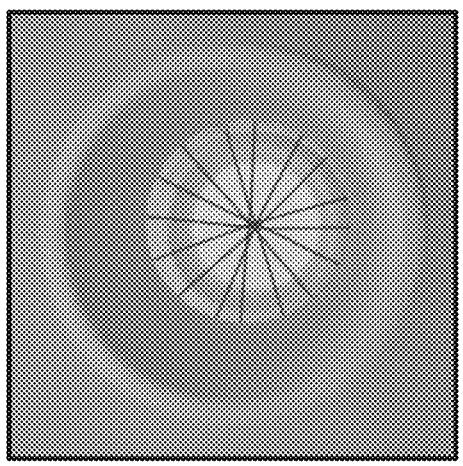
FIG. 4c is an absorbable vascular filter constructed from polydioxanone suture size 2-0 in a radial pattern typical of traditional IVC filters.
Figure 4D:
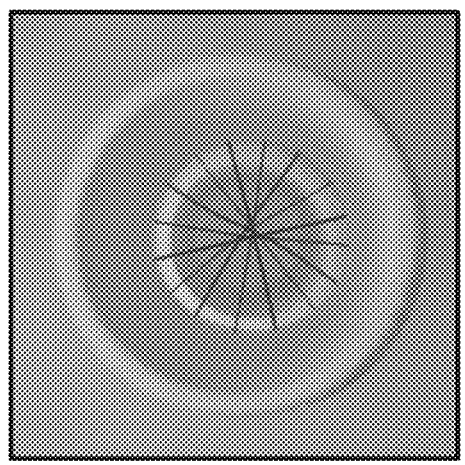
FIG. 4d is an absorbable vascular filter constructed from polydioxanone suture sizes 3-0, 2-0, 0, and 1 in a radial pattern that features sequential degradation based on the varying diameters of the capture elements.

FIG. 4a sports webbed capture elements that are purposely designed for sequential or phased absorption to avoid simultaneous detachment of the entire filter during absorption. Here varying diameter strands of polydioxanone (size 3-0, 2-0, 0 and 1) were utilized to vary the time to complete absorption, in addition to varying the expiration dates. Since the absorbable polymers initially break at the stress points during absorption, the webbed filters were designed to disintegrate into 8 pieces at length D/2, and 8 pieces sized D/4, where D is the inside diameter of the vessel. The objective is piecemeal disintegration, phased or sequential, to minimize free floating exposure of the polymer filter capture elements in circulation. FIG. 4b is the same webbed design but with uniformly sized polydioxanone suture for comparison. FIG. 4c is a radial filter design similar to conventional metal IVC filters yet sports the varying diameter sutures for sequential absorption. Finally, FIG. 4d is a radial design constructed exclusively with polydioxanone size 2-0.

The primary endpoint for evaluating the absorbable polymers for vascular filter application was load at break as a function of time. In addition to the absorbable filters pictured in FIG. 4, several test cells were fabricated with the various absorbable polymer candidates for weekly destructive tensile testing. Polymer characterization was performed utilizing the ADMET eXpert 7601 tensile testing machine with MTESTQuattro software (Norwood, Mass.) at weekly intervals to yield stress vs. strain graphs in addition to the primary endpoint of load at break, and several secondary endpoints: (i) maximum stress (tensile strength), (ii) maximum strain (% elongation at break), (iii) energy at break, and (iv) Young's modulus of elasticity. The ADMET machine was operated with a crosshead speed of 3 cm/min and outfitted with a high resolution 100 lb load cell and 2KN pneumatic grippers.

The candidate absorbable polymers (representing capture elements) sewn into the test cells were embedded in a closed circulation system engineered to mimic human cardio physiology. At weekly intervals, the system was shut down to extract sutures of each size and type to perform destructive tensile testing. As a control, identical absorbable sutures were submerged into a static buffer bath (StableTemp digital utility bath, Cole-Parmer, Vernon Hill, Ill.) held at 37° C. and also tested on a weekly basis. The hypothesis being that the increased thermodynamics of the circulation system accelerates both absorption rate and tensile strength loss of the capture elements.

The closed circulation system was constructed with thin walled ¾" PVC with od 26.7 mm that fit snug inside the flexible 25.4 mm id Tygon tubing that simulated the IVC. The heart of the system was a Harvard Apparatus large animal pulsatile blood pump (Holliston, Mass.) that simulated the ventricular action of the heart. The Harvard Apparatus blood pump was operated near continuously for 22 weeks (913K L pumped) with minor preventative maintenance.

The heart rate was adjusted to 60 bpm, stroke volume between 60 and 70 ml, systolic/diastolic duration ratio 35%/65%, and systolic blood pressure varied from 120 mmHg (simulated conditions for an arterial filter to prevent cerebral and systemic embolism) to 5 mmHg (simulated conditions for an IVC filter to prevent PE).

Real time measurements were available from the upstream and downstream sensor manifolds. The sensors upstream from the absorbable filters under test included digital temperature, flow rate (L/min), total flow (L), and pressure (mmHg). Downstream instrumentation included real time measurement of % oxygen, total dissolved solids (TDS in ppt), and pH. TDS monitoring was included to evaluate the absorption by-products less than 20 microns in size, while the downstream 80 micron in-line filter would catch fragments of suture from the filters and test cells.

The 4 candidate absorbable vascular filters introduced in FIG. 4 were installed in series along the upstream tubing, whereas 5 test cells containing absorbable suture for weekly destructive testing were installed in series along the downstream section of the in-vitro cardio test system. A 288W heating tape with thermostat was utilized to maintain 37° C. within the closed circulation system. Finally, the circulating fluid was pH 7.4 phosphate buffer (Invitrogen, Carlsbad, Calif.) with a similar electrolyte profile as human blood. Buffer was replaced weekly in an effort to maintain stable pH.

Absorption and tensile properties of the selected polymers were determined as a function of time until compete strength degradation in both the circulation system and control bath. The phosphate buffer in the circulation system was changed weekly as the pH decreased from 7.4 to an average 6.6 during each week. Buffer was changed in the control bath only monthly due to better pH stability in the static environment. Mean flow was 4.7 L/min while oxygen averaged 30% and TDS 8.8 ppt.

Figure 5:
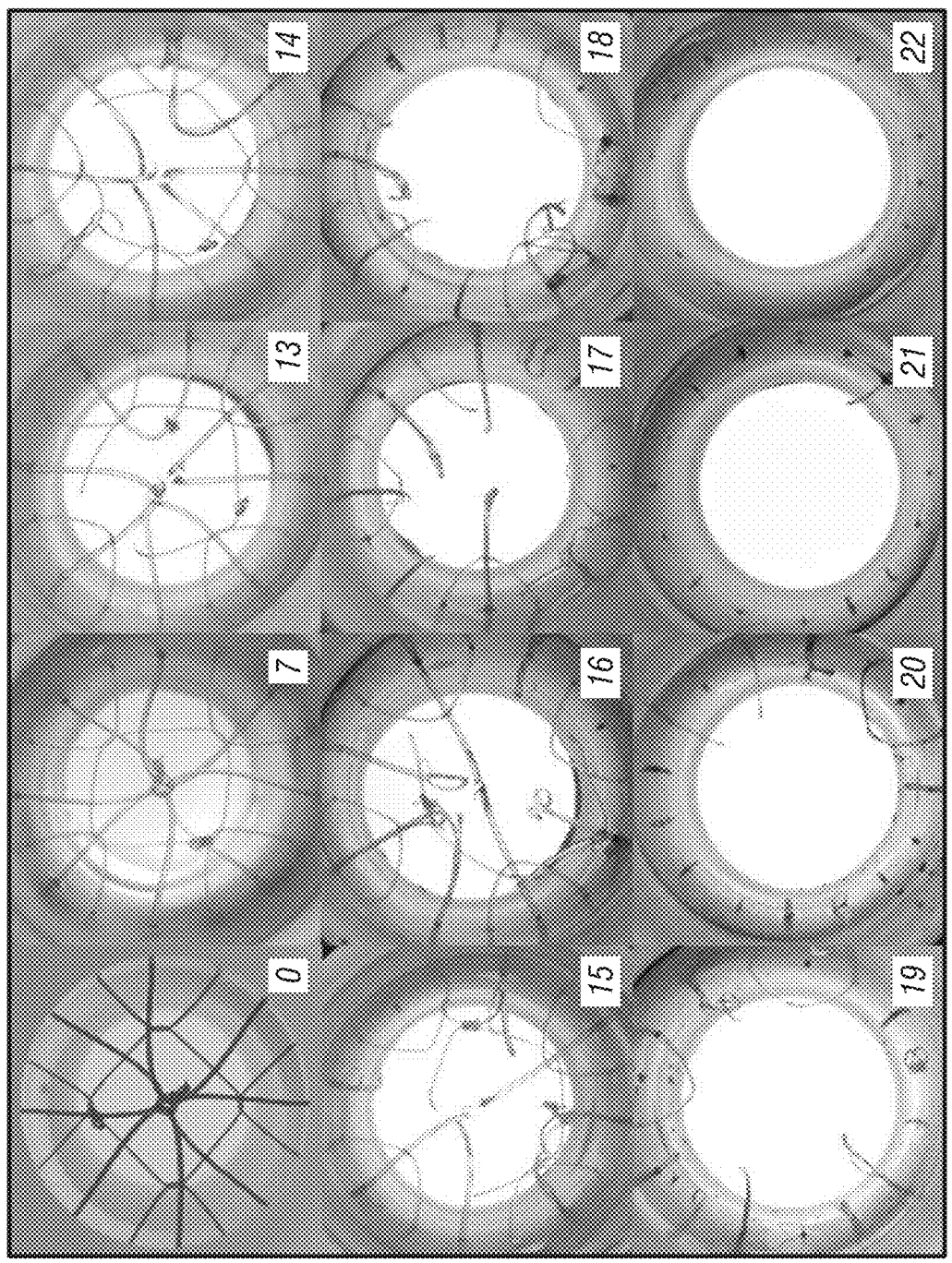
FIG. 5 displays photographs of the absorbable filter presented in FIG. 4a during in-vitro testing at weeks 0, 7, 13-22 to reveal the sequential degradation of the filter loosing 1 to 2 capture elements per week beginning in week 13 and reaching final disintegration by week 22.

The phased or sequential absorption of the webbed absorbable filter design is illustrated in the collage of FIG. 5. Notice the filter begins to disintegrate during the 13th week and continues in a phased manner, losing only 1 or 2 capture elements per week thereafter, until complete disintegration in 22 weeks. Initial fractures detected in the 13th week were located at the high stress points within the capture elements. Since the apex of a capture element mounted to the circumferential support experiences twice the stress in comparison to the base of the capture element, the initial break will be at the apex. The capture elements that formed loops extending from the vessel wall to the center of the filter were constructed of polydioxanone size 1 and 0 with expiration date January 2012, while the shorter capture elements that extended a quarter of the diameter were constructed of size 3-0 polydioxanone suture with an expiration date of January 2015. The expiration date was seen to play a greater role than suture diameter in the rate of absorption since the smaller diameter suture fractured in week 17, versus the larger diameter suture that fractured in week 13. The planned disintegration of 8 elements of length D/2 and 8 elements of length D/4 for the webbed filter actually yielded smaller brittle fragments due to splintering and fragmenting. In fact the largest filter element captured from the webbed design by the downstream 80 um filter revealed a maximum sized fragment of 5 mm×0.3 mm.

Figure 6:
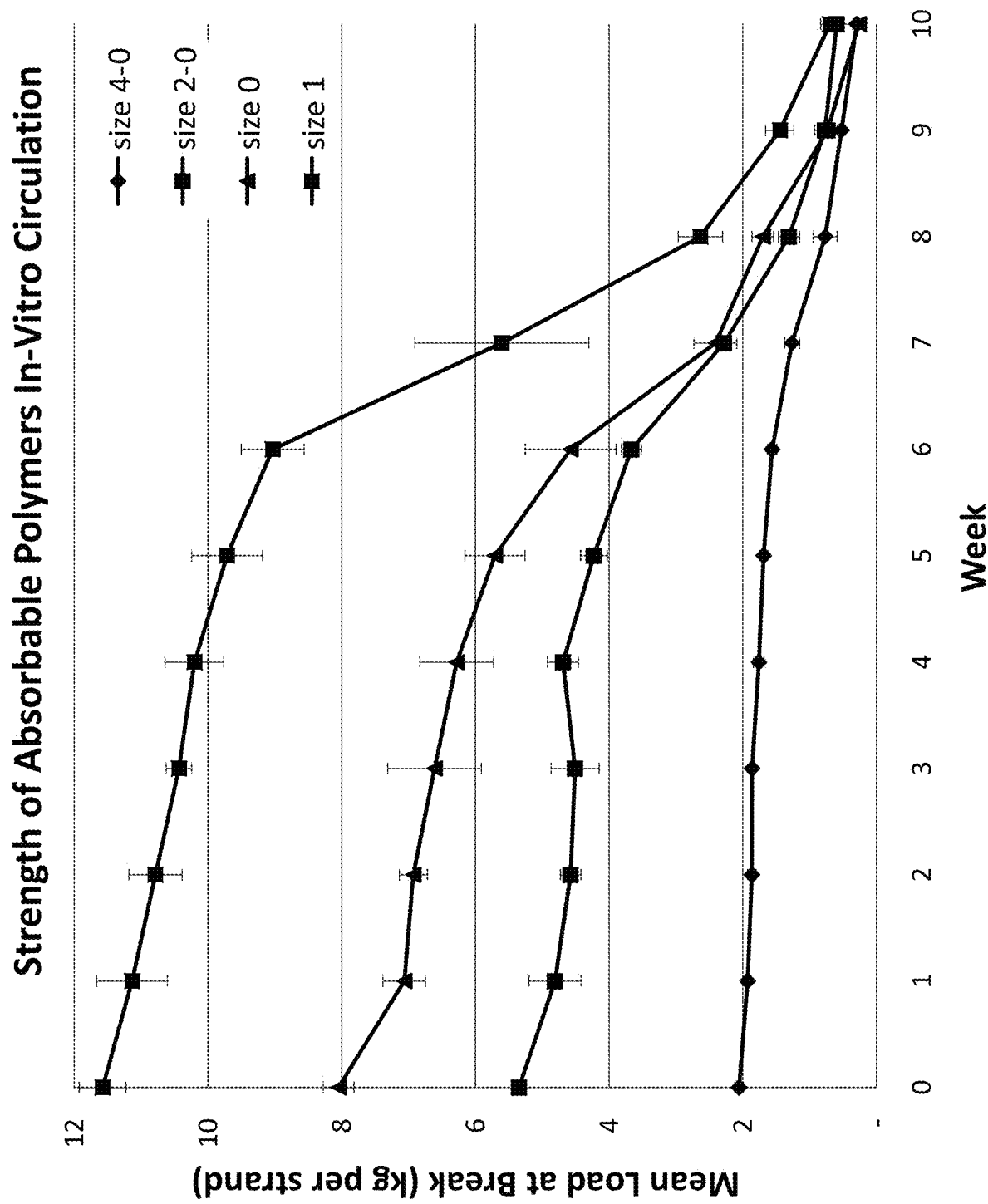
FIG. 6 is a graph of the mean load at break (kg/strand) of polydioxanone capture elements vs. time during the in-vitro testing.

Perhaps the paramount characteristic under consideration for use in an absorbable vascular filter is the strength retention profile of the absorbable polymers as depicted in FIG. 6 for polydioxanone in the in-vitro circulation system. As shown, polydioxanone initially exhibits moderate strength degradation, less than approximately 5% per week for the initial 5 to 6 weeks, followed by rapid decline approaching 20% per week thereafter. As a conservative summary for the initial 5 weeks in circulation, polydioxanone size 1 maintained about 10 kg strength, size 0 maintained 6 kg, size 2-0 maintained 4 kg, and size 4-0 maintained 1.5 kg. Similar results were obtained from a buffer bath control for the initial 5 weeks. However, statistical difference was achieved at week 5 for size 0 ($p<0.014$), week 6 for sizes 2-0 and 1 ($p<0.021$), and week 7 $p<0.011$).

The proposed filter designs employ multiple strands serving as capture elements, hence the emboli load is distributed across N strands. Therefore assuming equal distribution, the net emboli load that can be accommodated by the filter is a multiple, N, of the per strand load at break. Consequently, a polydioxanone size 2-0 filter with 8 capture elements secured at the circumferential support would accommodate a net emboli load of 32 kg.

Figure 7:
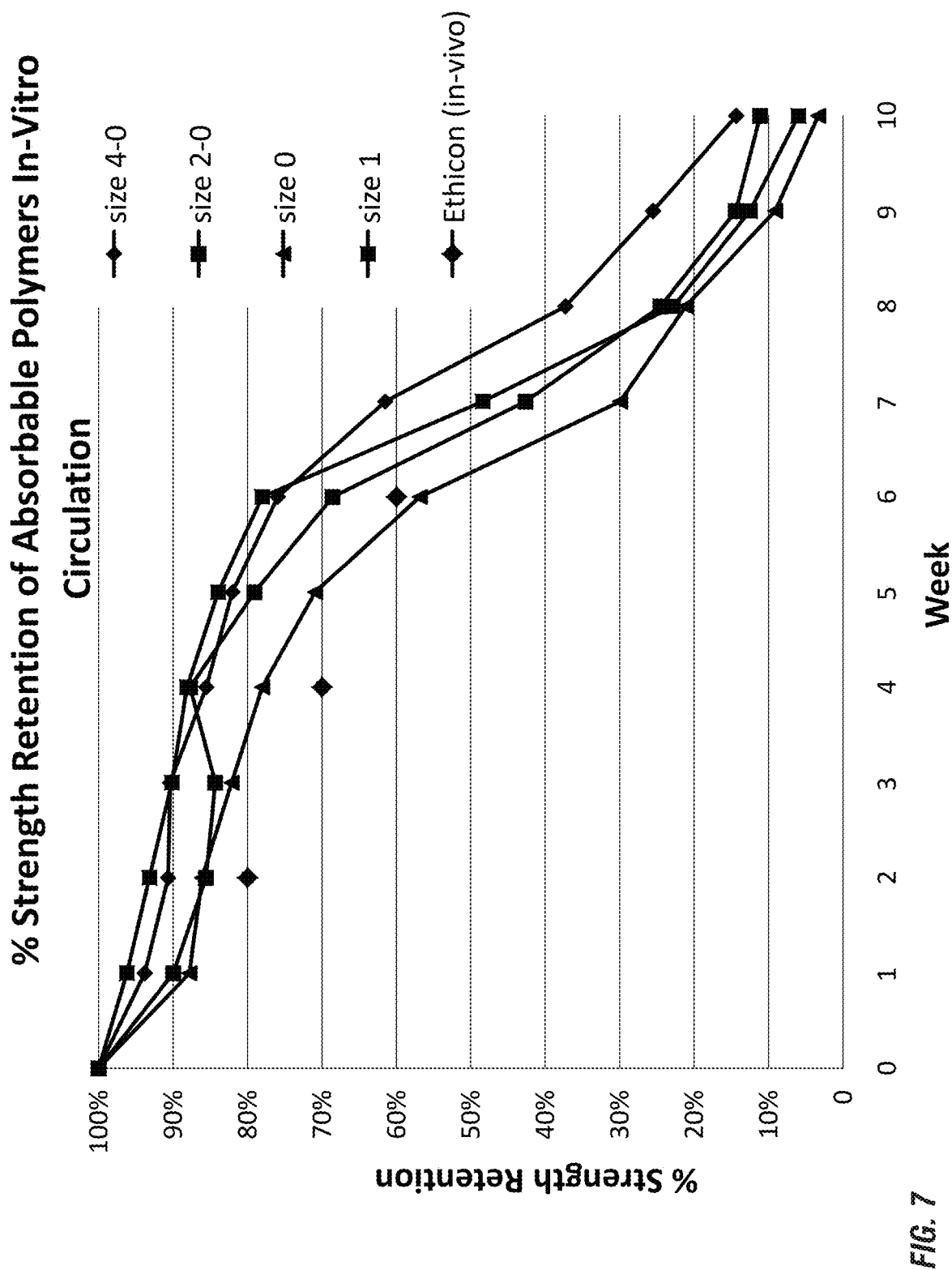
FIG. 7 is a graph of polydioxanone capture element strength retention as a percentage of the original strength vs. time.

An alternative method for accessing strength retention for the polymers is to chart the percentage strength retention as a function of time as shown in FIG. 7. Here all polydioxanone sizes slowly lost strength for the first 5 weeks, then rapidly absorbed to negligible strength by the 10th week. Specifically, polydioxanone within the in-vitro circulation system retained average strength for sizes 2-0 and larger of 88% at 2 weeks, 85% at 4 weeks, and 68% at 6 weeks vs. Ethicon's in-vivo animal tissue approximation applications that yielded 80% at 2 weeks, 70% at 4 weeks and 60% at 6 weeks per Ethicon product literature.

Figure 8:
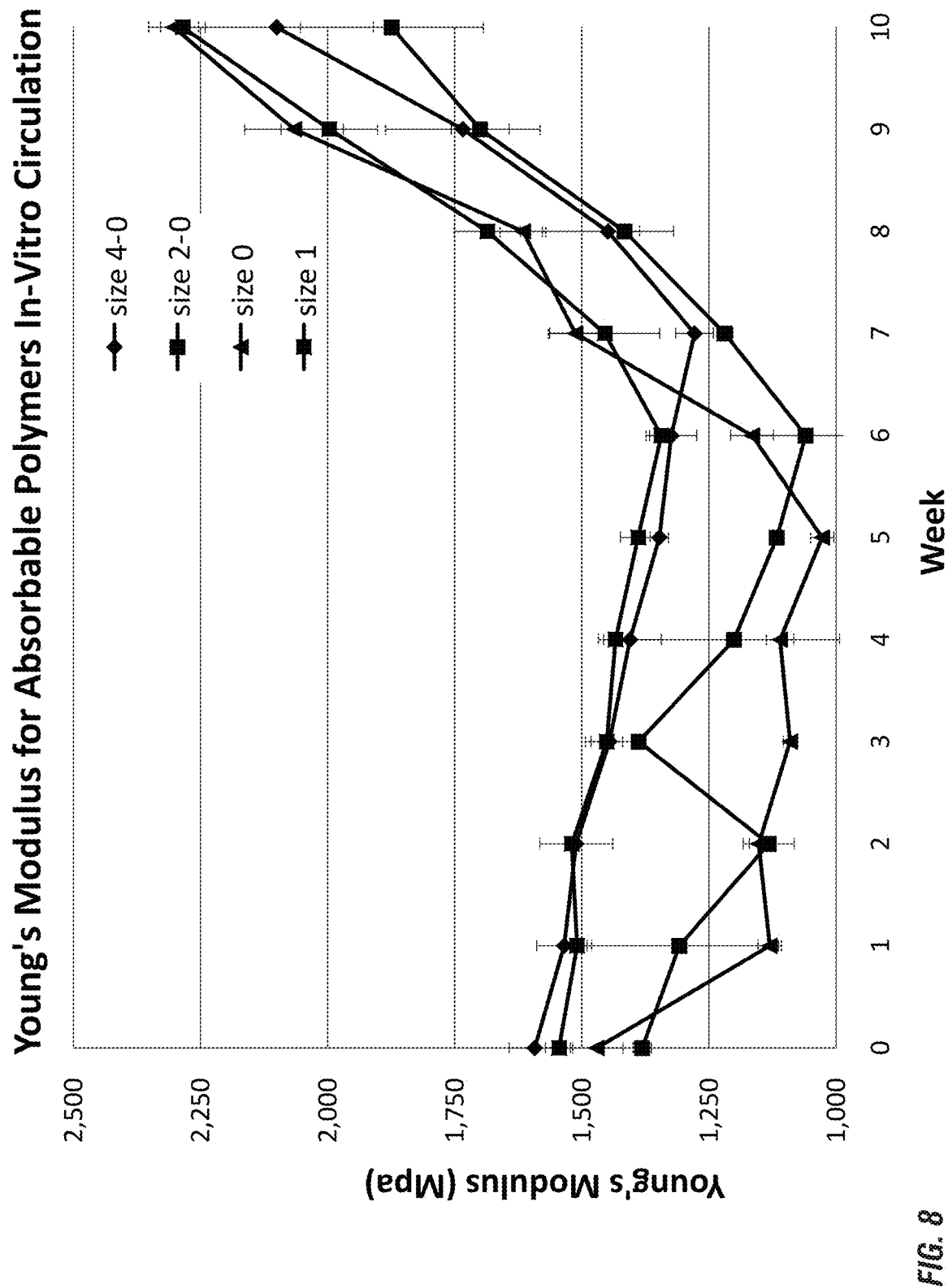
FIG. 8 is a graph of Young's modulus for polydioxanone capture elements vs. time during the in-vitro testing.

Young's modulus of elasticity ranged from 1.0-2.3 GPa for polydioxanone as shown in FIG. 8 for the absorbable filter elements. Notice that Young's modulus initially decreased (polymer became more elastic) as it was subjected to the buffer, reached a minimum at 6 weeks, then increased to approximately twice the initial value. This increase in Young's modulus for polydioxanone is indicative of the increased brittleness as it reached zero terminal strength, and was further observed during disintegration. This property may well be advantageous for the absorbable filter application. For example, as polydioxanone reached zero terminal strength and disintegrated, it splintered and fractured into smaller, brittle fragments thereby being potentially less harmful to downstream organs. Further studies are required to determine the exact size of the terminal fragments in-vivo and evaluate potential pulmonary micro-infarcts.

In conclusion from the in-vitro absorbable filter study, polydioxanone appears to be a strong candidate for absorbable vascular filters with sufficient strength retention to capture emboli for at least 6 weeks, then absorb rapidly over the next 16 weeks via hydrolysis into carbon dioxide and water. Specifically polydioxanone size 2-0 was shown to conservatively maintain 4 kg load at break per strand throughout 5 weeks in circulation. Hence a filter incorporating 8 capture elements would trap an embolus load of 32 kg; or equivalently, an embolism would have to deliver 1600 kgmm of energy to break through the filter which is highly unlikely given that the pressure in the IVC is a mere 5 mmHg (about 0.1 psi). Moreover, the webbed filter geometry with varied diameter capture elements and expiration dates was shown to disintegrate in a sequential or phased manner, releasing 1 or 2 small brittle filter fragments (less than 5 mm×0.3 mm each) weekly in circulation from weeks 14 through 22. Together with polydioxanone being FDA-approved and proven to be nonallergenic and nonpyrogenic, a catheter-deployed polydioxanone absorbable vascular filter would likely be an efficient and effective device for the prevention of pulmonary embolism.

A preferred installation of the absorbable vascular filter is via intravenous insertion with a catheter requiring only a local anesthetic as illustrated in FIGS. 9*a-e*. Here the filter is collapsed and compressed within a delivery catheter comprised of an outer sheath 71 and internal applicator or stabilizer piston 73 on a central rod as illustrated in FIG. 9*a*. For IVC filter deployment, the delivery catheter is inserted into the patient's vasculature of convenient location, such as the femoral vein or internal jugular. Subsequently, the delivery catheter is fed through the vasculature typically over a guide wire until reaching the desired deployment location, often inferior to the renal veins. Next the compressed filter 50 is allowed to expand upon sliding the exterior sheath 71 in the proximal direction while simultaneously pushing the stabilizer rod and piston 72 in the distal direction (refer FIG. 9*b*). Once the exterior sheath 71 is withdrawn away from the filter, the stabilizing piston 73 can also be retracted as depicted in FIG. 9*c*. Consequently as a thrombosis event releases an embolus 80, the embolus is captured by the vascular filter and is prevented from traveling to the heart and lungs thereby preventing a potentially fatal PE (refer FIG. 9*d*). Following the desired prophylactic time window for filter utilization (approximately 6 weeks in many applications), the filter is biologically absorbed resulting in the absence of any foreign material in the vessel as depicted in FIG. 9*e*.

Figure 10A:
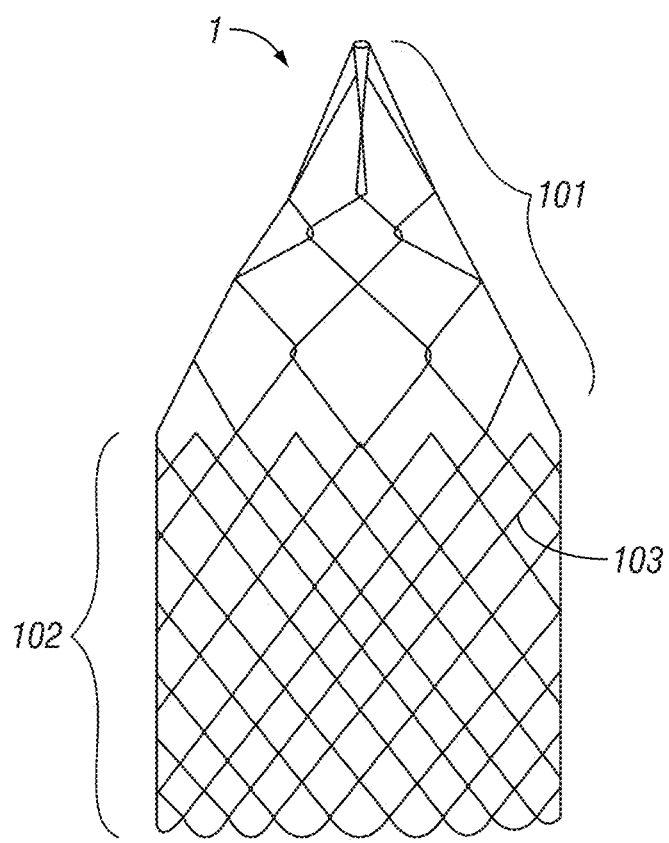
FIG. 10a represents an embodiment of the absorbable vascular filter constructed of a braided or woven stent integrated with a capture basket.
Figure 10B:
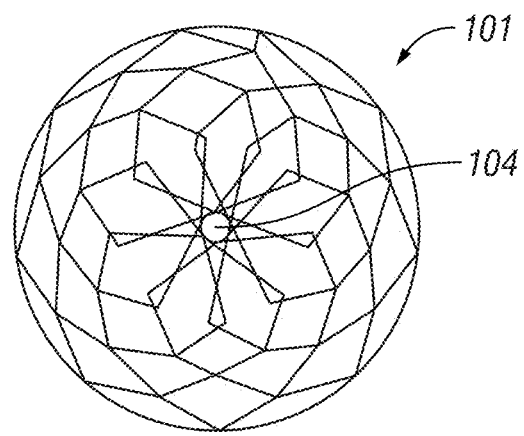

An alternative embodiment of the absorbable vascular filter 1 is portrayed in FIG. 10*a* with an integrated circumferential support 102 and capture basket 101. Here the circumferential support 102 and capture basket 101 are braided or woven much like a radial expansible stent that can be compressed in a catheter as described above prior to deployment. FIG. 10*b* is a top view of the absorbable vascular filter that displays the weave or braid of the capture basket 101. The weave is shown to maintain a patent center 104 to allow insertion of a guide wire during catheter deployment. The appeal of this particular embodiment is that the entire absorbable vascular filter (circumferential support and capture basket composed of the capture elements) can be fabricated from a single filament with a designed radial force to prevent filter migration as described below. In accordance with one or more embodiments, the circumferential support 102 may be characterized by a first lattice spacing and the capture basket 101 may be characterized by a second lattice spacing. The first lattice spacing may be smaller than the second lattice spacing.

The integrated absorbable vascular filter shown in FIGS. 10*a* and *b* yields a diametrically expandable and compressible tubular filter that exhibits a radial force with magnitude dependent on the materials chosen, angle phi ($\varphi$) of the crossing elements of the weave, and the amount of diameter over sizing employed. Specifically, the angle important to establishing radial force is depicted as $\varphi$ in FIG. 11. The larger the angle $\varphi$ as it approaches 180°, the greater the amount of radial force provided by the weave. Typically $\varphi$ is an obtuse angle, chosen between 90 and 180°.

For illustration, a simple cylindrical braided weave (L=7, P=4) is shown in FIG. 11 cut in the longitudinal direction and placed flat on a surface revealing the looping pins 110 and braiding filament 103. Considering the weave as a series of sinusoid waveforms of period P$\tau$ (see bold section of weave in FIG. 11), where P is the number of looping pins traversed for one cycle of the sinusoid and $\tau$ is the pin-to-pin spacing, an algorithm can be derived to ensure that for a given set of parallel looping pins L that equidistantly span the circumference of the intended diameter of the vascular filter, each pin will be looped once and the final loop ending at the origin.

The algorithm can be visualized by a table as shown in Table 1 to indicate the relationship between L, P and the angle φ for any desired number of circumferential loops (L).

TABLE 1

Relationship between braiding parameters.

| | L = 7 | | | | | | N | | | | | |
|---|---|---|---|---|---|---|---|---|---|---|---|---|
| phi | P | L/P | 1 | 2 | 3 | 4 | 5 | 6 | 7 | 8 | 9 | 10 |
| 41.0 | 2 | 3.50 | 3.50 | 7.00 | 10.50 | 14.00 | 17.50 | 21.00 | 24.50 | 28.00 | 31.50 | 35.00 |
| 73.6 | 4 | 1.75 | 1.75 | 3.50 | 5.25 | 7.00 | 8.75 | 10.50 | 12.25 | 14.00 | 15.75 | 17.50 |
| 96.6 | 6 | 1.17 | 1.17 | 2.33 | 3.50 | 4.67 | 5.83 | 7.00 | 8.17 | 9.33 | 10.50 | 11.67 |
| 112.5 | 8 | 0.88 | 0.88 | 1.75 | 2.63 | 3.50 | 4.38 | 5.25 | 6.13 | 7.00 | 7.88 | 8.75 |
| 123.7 | 10 | 0.70 | 0.70 | 1.40 | 2.10 | 2.80 | 3.50 | 4.20 | 4.90 | 5.60 | 6.30 | 7.00 |

L/P represents the fractional number of sinusoids traversed per circumference, and N represents the total number of turns around the circumference of the cylinder. Essentially the weave creates sinusoids that are out of phase by a fixed increment until the final loop is achieved for which the final sinusoid is desired to be in-phase with the initial sinusoid. The in-phase condition requires the product N×(L/P) to be an integer. Moreover, to ensure all pins are looped, the first integer to be formed by the product N×(L/P) must occur where N=P.

For example with L=7 and P=4, the first integer that appears in the row corresponding to P=4 of Table 1 is where N=4 so this combination of L, P, and N will provide a successful braid wherein all pins will be utilized (7 across the top, 7 across the bottom) and the final weave will terminate at the origin. It can be demonstrated that L must be an odd integer for a successful braid. It can further be shown that the angle φ can be expressed as $\varphi = 2\tan^{-1}(P\pi r/L1)$ where r and l is the radius and length of the desired filter circumferential support 102. The values for r and l used for calculating φ in Table 1 were 0.625 and 1.5 inches respectively. Also τ is easily computed from the relationship $L\tau = 2\pi r$ or $\tau = 2\pi r/L$.

Figure 12:
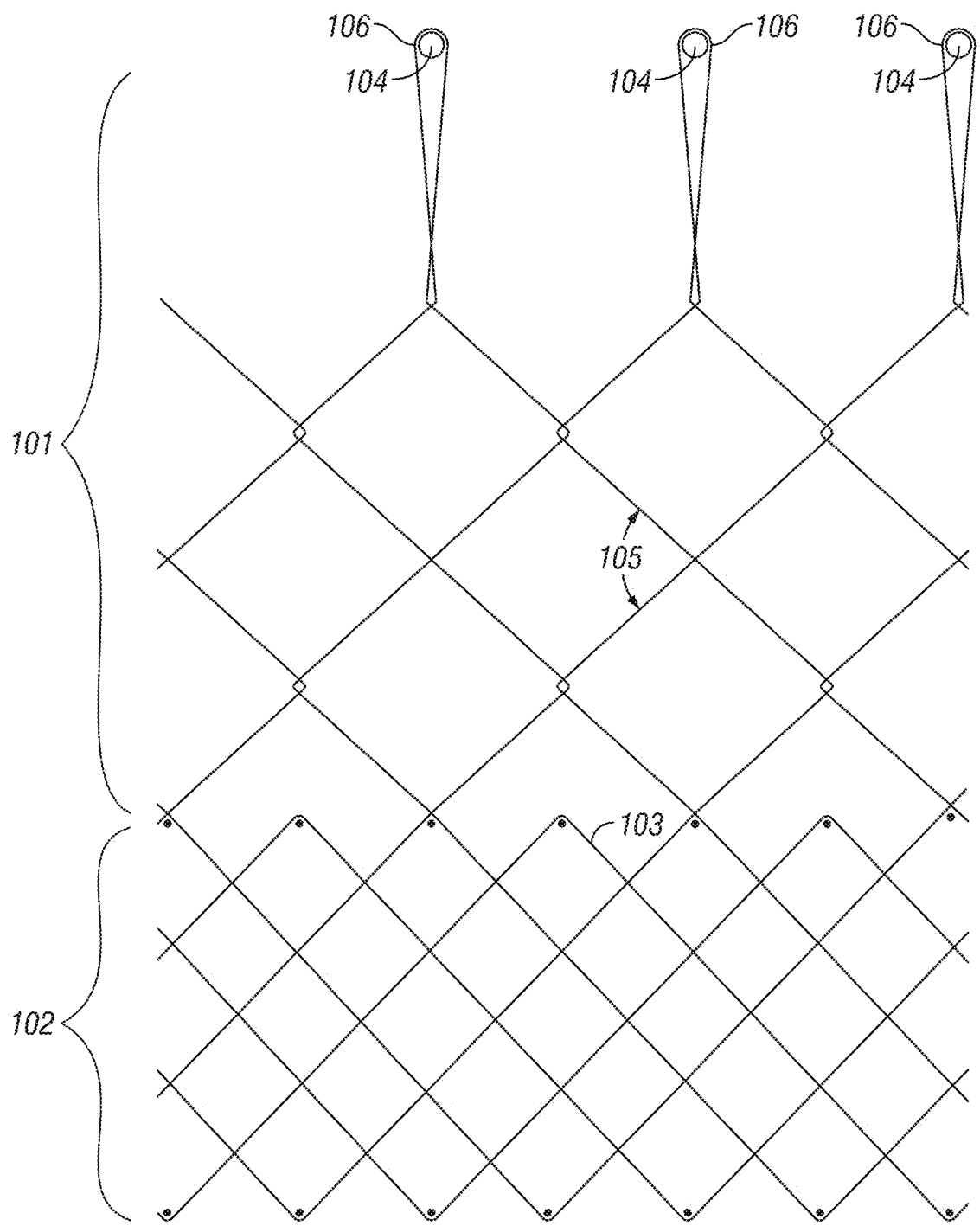
FIG. 12 is an expanded view of the braid or weave of absorbable elements comprising both the stent section and capture basket for the integrated absorbable vascular filter.

FIG. 12 depicts another braid combination where L=7 and P=6. Notice that the first integer to appear in the row for P=6 in Table 1 corresponds to N=6 hence the braid will terminate successfully at the origin and all L pins looped once. Further FIG. 12 illustrates a method for forming the capture basket 101 as a simple continuous extension of the filament beyond the circumferential support 102. As shown at the alternating looping points across the top of the circumferential support, the conical capture basket 101 is weaved by sequentially interlocking loops from adjacent loops 105 and extending a loop to the apex 106. The apical loops from each extension 106 can be bonded together revealing a conical capture basket as shown in FIG. 10b with a patent center apex 104. Clearly other braided patterns can be employed to yield the pattern resolution sufficient to trap emboli of a desired size.

Figure 13A:
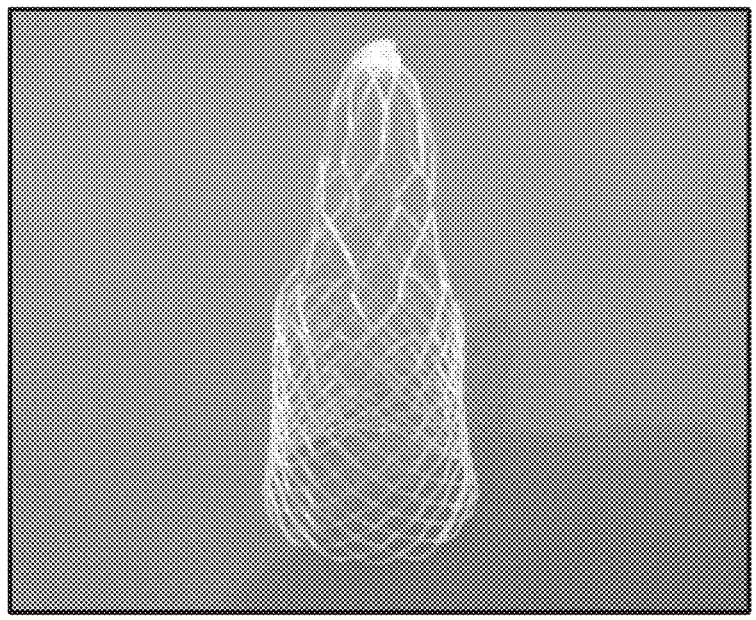
FIG. 13a is a photograph of an integrated absorbable IVC filter woven with a single synthetic filament.
Figure 13B:
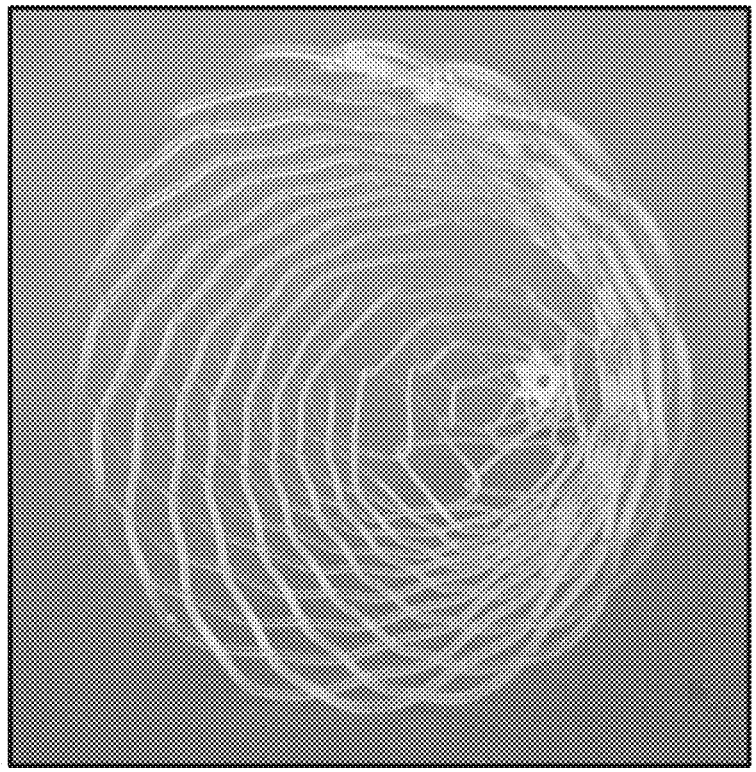

Although only a set of 7 looping pins were considered for simplicity in the above illustrations, a more likely number useful for an absorbable vascular filter for the IVC may well be 17 or 19 with φ>100°. Specifically, an absorbable IVC filter with integrated circumferential support and capture basket was fabricated with a single 10 ft synthetic filament (0.5 mm diameter) as shown in FIGS. 13a and b with L=17, P=16, φ=102°, l=1.5", r=0.625", and τ=0.23". The self expandable IVC filter provides sufficient radial force to maintain placement in the IVC by the choice of the obtuse weave angle, 25% oversized diameter (to fit 1" IVC diameter), and wide diameter filament (0.5 mm). Alternatively, the above described integrated absorbable vascular filter can be constructed with multiple bonded filaments, although a single continuous filament may be preferable.

Although the present invention has been described with reference to specific exemplary embodiments, it will be evident to one of ordinary skill in the art that various modifications and changes may be made to these embodiments without departing from the broader spirit and scope of the invention. Accordingly, the specification and drawings are to be regarded in an illustrative rather than a restrictive sense.

REFERENCES

[1] Goldhaber S Z, Ortel T L. The Surgeon General's Call to Action to Prevent Deep Vein Thrombosis and Pulmonary Embolism, Office of the Surgeon General (US), National Heart, Lung, and Blood Institute (US).Rockville (MD). 2008
[2] Spencer F A, Emery C, Lessard D, Anderson F, Emani S, Aragam J et al. The Worcester Venous Thromboembolism study; a population-based study of the clinical epidemiology of venous thromboembolism. J Gen Intern Med 2006 July; 21 (7); 722-7.
[3] Bick R L. Hereditary and acquired thrombophilia: preface. SeminThrombHemost 1999; 25; 251-3.
[4] Agudelo J F, Morgan S J, Smith W R. Venous Thromboembolism in Orthopedic Trauma Patients, Orthopedics. 2005 October; 28(10):1164-71.
[5] Tapson V F. Acute pulmonary embolism. N Engl J Med, 2008, 358, 10. 1037-52.
[6] Goldhaber S Z, Visani L, De Rosa M. Acute P E: clinical outcomes in the International Cooperative PE Registry (ICOPER). Lancet 1999. 353. 1386-9.
[7] Geerts W H, Jay R M, Code Kl, et al. A comparison of low-dose heparin with low-molecular weight heparin as prophylaxis against venous thromboembolism after major trauma. N Engl J. Med. 1996; 335:701-7.
[8] Silverstein D M, Heit J A, Mohr D N, Petterson T M, O'Fallon W M, Meltron L J, $3^{rd}$. Trends in the incidence of deep vein thrombosis and pulmonary embolism: a 25-year population-based study. Arch Intern Med 1998; 158(6). 585-93.
[9] Von V R. Weitereuntersuchungenueber die verstopfung der lungenarterien and ihrefolge. Traube's Beitraegeexp Path u Physiol, 1846; 2:21-31.
[10] Goldhaber S Z, Savage D D, Garrison R J, et al. Risk factors for pulmonary embolism: The Framingham Study. Am J. Med. 1983; 74: 1023-1028.

[11] Coon W W. Epidemiology of venous thromboembolism. Ann Surg. 1977; 186:149-164.

[12] Muntz J E, Michota F A. Prevention and management of venous thromboembolism in the surgical patient: options bye surgery type and individual patient risk factors, Am J of Surg, 2010; 199, S11-20.

[13] American Academy of Orthopaedic Surgeons Clinical Guideline on Prevention of Pulmonary Embolism in Patients Undergoing Total Hip or Knee Arthroplasty, American Academy of Orthopaedic Surgeons, May 2007.

[14] Pulmonary Embolism Prevention (PEP) Trial Collaborative Group: Prevention of pulmonary embolism and DVT with low dose aspirin: pulmonary embolism prevention (PEP) trial. Lancet. 2000; 355: 1295-1302

[15] Prins M H, Hutten B A, Koopman M M, et al. Longterm treatment of venous thromboembolic disease. Thromb Haemost 1999; 82:892-8.

[16] Tran H, McRae S, Ginsberg J. Anticoagulant Treatment of Deep Vein Thrombosis and Pulmonary Embolism. Cardiology Clinics, 2008, 26, 235-50.

[17] Morgan S J, Jeray K J, Phieffer L S, Grisby J H, Bosse M J, Kellam J F. Attitudes of orthopaedic trauma surgeons regarding current controversies in the management of pelvic and acetabular fractures. J Orthop Trauma. 2001; 15:526-32.

[18] Meissner M H, Chandler W L, Elliot J S. Venous thromboembolism in trauma: a local manifestation of systemic hypercoagulability? J. Trauma. 2003; 4:224-31.

[19] Geerts W H, Bergqvist D, Pineo G F, et al. Prevention of venous thromboembolism: American College of Chest Physicians evidence-based clinical practice guidelines (8th edition). Chest. 2008; 133:381 S-453S.

[20] Huo M H, Spyropoulos A C. The eighth American college of chest physicians guidelines on venous thromboembolism prevention: implications for hospital prophylaxis strategies. J Thromb Thrombolysis. 2011, February; 31(2): 196-208.

[21] Baglin T P, Brush J, Streiff M. Guidelines on the use of vena cava filters. British Committee for Standard in Haematology, British J of Haematology, 2006, 134, 590-5.

[22] Rogers F B, Cipolle M D, Velmahos G, et al. Practice management guidelines for the prevention of venous thromboembolism in trauma patients: the East practice management guidelines work group. J. Trauma. 2002; 53:142-164.

[23] Rosenthal D, Wellons E D, Lai K M, et al. Retrievable inferior venal cava filters: initial clinical results. Ann Vasc Surg 2006; 20:157-165.

[24] Gosin I S, Graham A M, Ciocca R G, et al. Efficacy of prophylactic vena cava filters in high risk trauma patients. Ann Vasc Surg 1997; 11:100-05.

[25] Spain D A, Richardson J D, Polk H C, et al. Routine prophylactic vena cava filter insertion in severely injured patients decreases the incidence of pulmonary embolism. J Am Coll Surg 1995; 180:641-47.

[26] Stein P D, Kayali F, Olson R E. Twenty-one year trends in the use of inferior vena cava filters. Arch Intern Med 2004; 164:1541-5.

[27] Kaufman J A, Kinney T B, Streiff M D, et al. Guidelines for the use of retrievable and convertible vena cava filters: report from the Society of Interventional Radiology multidisciplinary consensus conference. J Vasc Intery Radiol. 2006; 17:449-459.

[28] Rodriquez J L, Lopez J M, Proctor M C, et al. Early placemen of prophylactic vena cava filters in injured patients at high risk for pulmonary embolism. J. Trauma. 1996; 40:797-804.

[29] Langan E M III, Miller R S, Caset W J III, Carsten C G III, Graham R M, Taylor S M. Prophylactic inferior vena cava filters in trauma patients at high risk: follow-up examination and risk/benefit assessment. J Vasc Surg. 1999; 30:484-90.

[30] Greenfield L J, Proctor M C, Rodriquez J L, Luchette F A, Cipolle M D, Cho J. Posttrauma thromboembolism prophylaxis. J. Trauma. 1997, 42:100-03.

[31] Young T, Tang H, Hughes R. Vena cava filters for the prevention of pulmonary embolism (Review). The Cochrane Library 2010, Issue 2.

[32] Decousus H, Leizorovics A, Parent F, et al. A clinical trial of vena caval filters in the prevention of pulmonary embolism in patients with proximal deep-vein thrombosis, N England J. Med. 338, 7:409-15.

[33] The PREPIC Study Group. Eight-year follow-up of patients with permanent vena cava filters in the prevention of pulmonary embolism: the PREPIC randomized study. Circulation 2005; 112:416-22.

[34] Ray C E, Kaufman J A. Complications of vena cava filters. Abdom Imaging 1996; 21:368-74.

[35] Ballew K A, Philbrick J T, Becker D M. Vena cava filter devices. Clin Chest Med 1995; 16:295-305.

[36] Streiff M B. Vena cava filters: a comprehensive review. Blood 2000; 95:3669-77.

[37] Pons M, Riglietti A, van den Berg J C. The role of vena cava filters in the management of venous thromboembolism. J Cardiovasc Surg 2010; 51: 355-64.

[38] Usoh F, Hignorani A, Ascher E, et al. Long-term follow-up for superior vena cava filter placement. Ann Vasc Surg. 2009; 23:350-4.

[39] Turba U C, Arsian B, Meuse M, et al. Gunther Tulip filter retrieval experience: predictors of successful retrieval. Cardiovasc Intervent Radiol. 2009

[40] Kinney T B. Update on inferior vena cava filters. J Vasc Intery Radiol. 2003; 14:425-40.

[41] Grande W J, Trerotola S O, Reilly P M, et al. Experience with the recovery filter as a retrievable inferior vena cava filter. J Vasc Intery Radiol 2005; 16:1189-93.

[42] Kirilcuk N N, Herget E J, Dicker R A, et al. Are temporary inferior vena cava filters really temporary? Am J Surg 2005; 190:858-63.

[43] Kumar B C, Chakraverty Z, Zealley I. Failed retrieval of potentially retrievable IVC filters: a report of two cases. Cardiovasc Intervent Radiol 2006; 29: 126-7.

[44] Removing Retrievable Inferior Vena Cava Filters: Initial Communication. FDA Division of Small Manufacturers, International and Consumer Assistance, Aug. 9, 2010.

[45] Nicholson W, Nicholson W J, Tolerico P, et al. Prevalence of fracture and fragment embolization of Bard retrievable vena cava filters and clinical implications including cardiac perforation and tamponade. Arch Intern Med. 2010.

[46] Karmy-Jones R, Jurkovich G H, Velmahos G C, et al. Practice patterns and outcomes of retrievable vena cava filters in trauma patients: an AAST multicenter study. J. Trauma. 2007; 62: 17-25.

[47] Tschoe M, Kim H S, Brotman D J, et al. Retrievable vena cava filters: a clinical review. J Hosp Med 2009, 4; 7: 441-8.

[48] Dabbagh O, Nagam N, Chitima-Matsiga R, et al. Retrievable inferior vena cava filters are not getting retrieved Where is the gap? Thrombosis Rsch 2010. 126: 493-7.

What is claimed is:

1. An absorbable filter fabricated with an absorbable polymeric filament that is configured for intra vena cava deployment comprising:
a sufficiently rigid polymeric circumferential element for attaching or securing the filter to a vessel, wherein the sufficiently rigid polymeric circumferential element is woven from the absorbable polymeric filament forming an obtuse weave angle that provides sufficient radial force to maintain placement in the vessel; and
a plurality of polymeric absorbable capture elements affixed to the sufficiently rigid polymeric circumferential element for capturing or retarding substances flowing in the vessel for a limited duration in time, the polymeric absorbable capture elements are configured from said absorbable polymeric filament;
wherein the sufficiently rigid polymeric circumferential element is characterized by a first lattice spacing and the polymeric absorbable capture elements are characterized by a second lattice spacing, the first lattice spacing being smaller than the second lattice spacing;
wherein individual ones of the plurality of polymeric absorbable capture elements are linked with adjacent polymeric absorbable capture elements to establish the second lattice spacing, and
wherein the sufficiently rigid polymeric circumferential element is braided to offer diametrically expandable and compressible tubular characteristics, and configured to be collapsed and compressed to a size that facilitates percutaneous intravascular vena cava deployment of the filter to a diameter of 16 mm or larger after the collapsed and compressed filter passes through the femoral or jugular vein within a catheter.

2. An absorbable filter, comprising:
a sufficiently rigid polymeric absorbable circumferential element for attaching or securing the filter to a vessel, the sufficiently rigid polymeric absorbable circumferential element being made from an absorbable polymeric filament that provides sufficient radial force to maintain filter placement in the vessel; and
an absorbable polymeric capture basket affixed to the sufficiently rigid polymeric absorbable circumferential element for capturing or retarding substances flowing in a vessel for a limited duration in time;
wherein the sufficiently rigid polymeric absorbable circumferential element is characterized by a first lattice spacing woven from the absorbable polymeric filament forming an obtuse weave angle and the absorbable polymeric capture basket is characterized by a second lattice spacing, the first lattice spacing being smaller than the second lattice spacing;
wherein the absorbable polymeric capture basket is formed by one or more filaments such that individual filament segments are linked with adjacent filament segments to establish the second lattice spacing; and
wherein the sufficiently rigid polymeric absorbable circumferential element is braided to offer diametrically expandable and compressible tubular characteristics, and configured to be collapsed and compressed to a size that facilitates percutaneous intravascular vena cava deployment of the filter to a diameter of 16 mm or larger after the collapsed and compressed filter passes through the femoral or jugular vein within a catheter.

3. The filter of claim 2, wherein the absorbable polymeric capture basket is fabricated from polymeric filaments selected from the group consisting of polypropylene, polypropylene encapsulated in polydioxanone, polypropylene co-knitted with polyglycolic acid fibers, polyethylene terephathalate, ePTFE, polydioxanone, polytrimethylene carbonate, polyglactin, polyglycolic acid, poly L lactic acid, poliglecaprone, polyglytone, and polylacticoglycolic acid.

4. The filter of claim 2, wherein the absorbable polymeric capture basket is a biocompatible mesh.

5. The filter of claim 2, wherein the absorbable polymeric capture basket is fabricated from a biocompatible mesh configured from a polymeric filament selected from the group consisting of polypropylene, polypropylene encapsulated by polydioxanone, polypropylene co-knitted with polyglycolic acid fibers, polyethylene terephathalate, and ePTFE.

6. The filter of claim 2, wherein the sufficiently rigid polymeric absorbable circumferential element is fabricated of an absorbable polymeric filament selected from the group consisting of polydioxanone, polytrimethylene carbonate, polyglactin, polyglycolic acid, poly L lactic acid, poliglecaprone, polyglytone, or polylacticoglycolic acid.

7. The filter of claim 2, wherein the sufficiently rigid polymeric absorbable circumferential element comprises an anchor element or barb for attachment to a vessel.

8. The filter of claim 2, wherein the sufficiently rigid polymeric absorbable circumferential element and/or the absorbable polymeric capture basket contains a bioactive surface for anticoagulation.

9. An absorbable filter comprising
a sufficiently rigid circumferential element fabricated from a fully absorbable polymeric filament that provides sufficient radial force for attaching or securing the filter to a vessel and to maintain filter placement in the vessel, the sufficiently rigid circumferential element integrated with an absorbable capture basket for capturing or retarding substances flowing in a vessel for a limited duration in time;
wherein the absorbable filter is configured for intra vena cava deployment;
wherein the sufficiently rigid circumferential element is fabricated from the absorbable polymeric filament forming an obtuse weave angle creating a first lattice spacing and the absorbable capture basket is characterized by a second lattice spacing, the first lattice spacing being smaller than the second lattice spacing;
wherein the absorbable capture basket is formed by one or more polymeric filaments such that individual filament segments are linked with adjacent filament segments to establish the second lattice spacing; and
wherein the sufficiently rigid circumferential element is braided to offer diametrically expandable and compressible tubular characteristics, and configured to be collapsed and compressed to a size that facilitates percutaneous intravascular vena cava deployment of the filter to a diameter of 16 mm or larger after the collapsed and compressed filter passes through the femoral or jugular vein within a catheter.

10. The filter of claim 9, wherein the sufficiently rigid circumferential element and absorbable capture basket are constructed of a single, continuous polymeric absorbable filament.

11. The filter of claim 9, wherein the sufficiently rigid circumferential element and the absorbable capture basket are constructed of a plurality of polymeric absorbable filaments.

12. The filter of claim 9, wherein the integrated sufficiently rigid circumferential element and the absorbable capture basket are fabricated from absorbable materials selected from the group consisting of polydioxanone, polytrimethylene carbonate, polyglactin, polyglycolic acid, poly L lactic acid, poliglecaprone, polyglytone, and polylacticoglycolic acid.

13. The filter of claim 9, wherein the sufficiently rigid circumferential element is woven from the absorbable polymeric filament forming an obtuse weave angle to offer diametrically expandable and compressible tubular characteristics to accommodate minimally invasive deployment via the catheter.

14. The filter of claim 9, wherein the radial force of the sufficiently rigid circumferential element exerted on the vessel is selected based on the angle of intersection of said absorbable polymeric filament that forms an obtuse weave angle comprising the sufficiently rigid circumferential element.

15. The filter of claim 9, wherein the absorbable capture basket is formed by sequentially interlocking loops from adjacent loops distal to the sufficiently rigid circumferential element and extending loops to an apex in a periodic manner to form a conical capture basket with filter resolution determined by the periodicity of a braid formed by the sequentially interlocking and extending loops.

16. The filter of claim 9, wherein the sufficiently rigid circumferential element and/or the absorbable capture basket contains a bioactive surface for anticoagulation.

17. A method for delivering a filter as claimed in claims 1, 2, or 9 with the catheter, wherein the delivery comprises
collapsing and compressing the sufficiently rigid circumferential element and the capture basket or the plurality of polymeric absorbable capture elements to the size that facilitates percutaneous intra vena cava deployment of the filter after the compressed and collapsed filter passes through the femoral or jugular vein within the catheter;
inserting the filter, in collapsed and compressed form, within the catheter to a desired position within a vessel; and
deploying the filter in expanded form at the desired position within a vessel to the diameter of 16 mm or larger; and
subsequently removing the catheter from the vessel.

* * * * *